(12) United States Patent
Urrea

(10) Patent No.: US 9,101,410 B1
(45) Date of Patent: Aug. 11, 2015

(54) FACET JOINT FUSION DEVICE AND METHOD FOR USING SAME

(76) Inventor: Robert E. Urrea, El Paso, TX (US)

( * ) Notice: Subject to any disclaimer, the term of this patent is extended or adjusted under 35 U.S.C. 154(b) by 1630 days.

(21) Appl. No.: 12/258,040

(22) Filed: Oct. 24, 2008

Related U.S. Application Data

(60) Provisional application No. 60/982,234, filed on Oct. 24, 2007.

(51) Int. Cl.
*A61B 17/70* (2006.01)

(52) U.S. Cl.
CPC ................................. *A61B 17/7064* (2013.01)

(58) Field of Classification Search
CPC .................................................. A61B 17/7064
USPC ...................... 606/246–249; 623/17.11–17.16
See application file for complete search history.

(56) References Cited

U.S. PATENT DOCUMENTS

| | | | |
|---|---|---|---|
| 5,067,957 A | 11/1991 | Jervis | |
| 5,702,453 A | 12/1997 | Rabbe et al. | |
| 5,713,899 A * | 2/1998 | Marnay et al. | 623/17.11 |
| RE36,758 E | 6/2000 | Fitz | |
| 6,258,115 B1 | 7/2001 | Dubrul | |
| 6,440,131 B1 * | 8/2002 | Haidukewych | 606/60 |
| 6,981,975 B2 | 1/2006 | Michelson | |
| 7,033,394 B2 | 4/2006 | Michelson | |
| 7,285,134 B2 * | 10/2007 | Berry et al. | 623/17.11 |
| 7,744,630 B2 * | 6/2010 | Lancial | 606/247 |
| 8,070,782 B2 * | 12/2011 | McKay | 606/279 |
| 8,894,685 B2 * | 11/2014 | Mickiewicz et al. | 606/247 |
| 2001/0021851 A1 * | 9/2001 | Eberlein et al. | 606/69 |
| 2001/0037112 A1 * | 11/2001 | Brace et al. | 606/69 |
| 2002/0016595 A1 * | 2/2002 | Michelson | 606/73 |
| 2002/0128717 A1 | 9/2002 | Alfaro et al. | |
| 2003/0088251 A1 | 5/2003 | Braun et al. | |
| 2003/0105462 A1 * | 6/2003 | Haider | 606/69 |
| 2003/0176925 A1 * | 9/2003 | Paponneau | 623/17.16 |
| 2004/0087948 A1 * | 5/2004 | Suddaby | 606/61 |
| 2004/0111093 A1 | 6/2004 | Chappuis | |
| 2004/0127906 A1 | 7/2004 | Culbert et al. | |
| 2005/0033431 A1 | 2/2005 | Gordon et al. | |
| 2005/0124993 A1 | 6/2005 | Chappuis | |
| 2006/0004367 A1 | 1/2006 | Alamin et al. | |
| 2006/0036322 A1 | 2/2006 | Reiley | |
| 2006/0036323 A1 | 2/2006 | Carl et al. | |

(Continued)

OTHER PUBLICATIONS

Jason C. Eck, DO, MS, et al., Minimally Invasive Lumbar Spinal Fusion, Journal of the American Academy of Orthopaedic Surgeons, Jun. 2007, p. 321-329, vol. 15 No. 6, U.S.

(Continued)

*Primary Examiner* — Jan Christopher Merene
(74) *Attorney, Agent, or Firm* — Patzik, Frank & Samotny Ltd.

(57) ABSTRACT

An encircling device for promoting arthrodesis of a cervical, thoracic and/or lumbar facet joint. The fusion can occur through the device as well as around and/or through the facet joint. The top cap may include a container where bone promoting substances are placed. A top cap may be placed within, around or over the top of the encircling device and affixed thereto using a variety of different fixation devices. In addition, the encircling device and/or top cap may be secured using a fastener or anchor such as a screw or other member to a interspinous process spacer, pedicle, pars interarticularis, spinous process, sacral ala, lamina, facet articular process, transverse process or other spinal bony anatomy.

38 Claims, 20 Drawing Sheets

(56) References Cited

U.S. PATENT DOCUMENTS

| | | |
|---|---|---|
| 2006/0058791 A1 | 3/2006 | Broman et al. |
| 2006/0111779 A1 | 5/2006 | Petersen |
| 2006/0111780 A1 | 5/2006 | Petersen |
| 2006/0111781 A1 | 5/2006 | Petersen |
| 2006/0111782 A1 | 5/2006 | Petersen |
| 2006/0190081 A1* | 8/2006 | Kraus et al. ............... 623/17.11 |
| 2006/0195091 A1 | 8/2006 | McGraw et al. |
| 2006/0200137 A1 | 9/2006 | Soboleski |
| 2006/0217715 A1 | 9/2006 | Serhan et al. |
| 2006/0217725 A1* | 9/2006 | Suh ................................ 606/71 |
| 2006/0235391 A1 | 10/2006 | Sutterlin, III |
| 2007/0073395 A1* | 3/2007 | Baumgartner et al. ..... 623/17.11 |
| 2007/0112428 A1* | 5/2007 | Lancial ...................... 623/17.12 |
| 2007/0250166 A1* | 10/2007 | McKay ...................... 623/17.11 |
| 2007/0255408 A1 | 11/2007 | Castleman et al. |
| 2008/0071379 A1 | 3/2008 | Rydell et al. |
| 2008/0125813 A1* | 5/2008 | Erickson et al. ............... 606/246 |
| 2008/0161927 A1 | 7/2008 | Savage et al. |
| 2008/0234735 A1* | 9/2008 | Joshi ............................ 606/247 |
| 2008/0255622 A1* | 10/2008 | Mickiewicz et al. ......... 606/319 |
| 2009/0099602 A1 | 4/2009 | Aflatoon |
| 2009/0112264 A1 | 4/2009 | Lins |

OTHER PUBLICATIONS

TrueFUSE Facet Fusion Allografts Frequently Asked Questions, with copyright notices of © MinSurg Corporation, 2006 and © 2006 Orthopedic Development Corporation.

Tov Vestgarden, MS et al., TruFUSE Facet Fusion Allograft, with a copyright notice of © MinSurg Corporation, 2006.

TrueFuse Fuse Facet Fusion Allografts product sheet, date unknown.

A Patent's Guide to Anterior Lumbar Fusion with Cages, with a copyright notice of © MMG 2002 found at http://www.orthogate.org.

Pedicle Screw Fixation Enhances Anterior Lumbar Interbody Fusion with Porous Tantalum Cages: An Experimental Study in Pigs, SPINE, with a copyright notice of © 2005 Lippincott Williams & Wilkins, Inc.

* cited by examiner

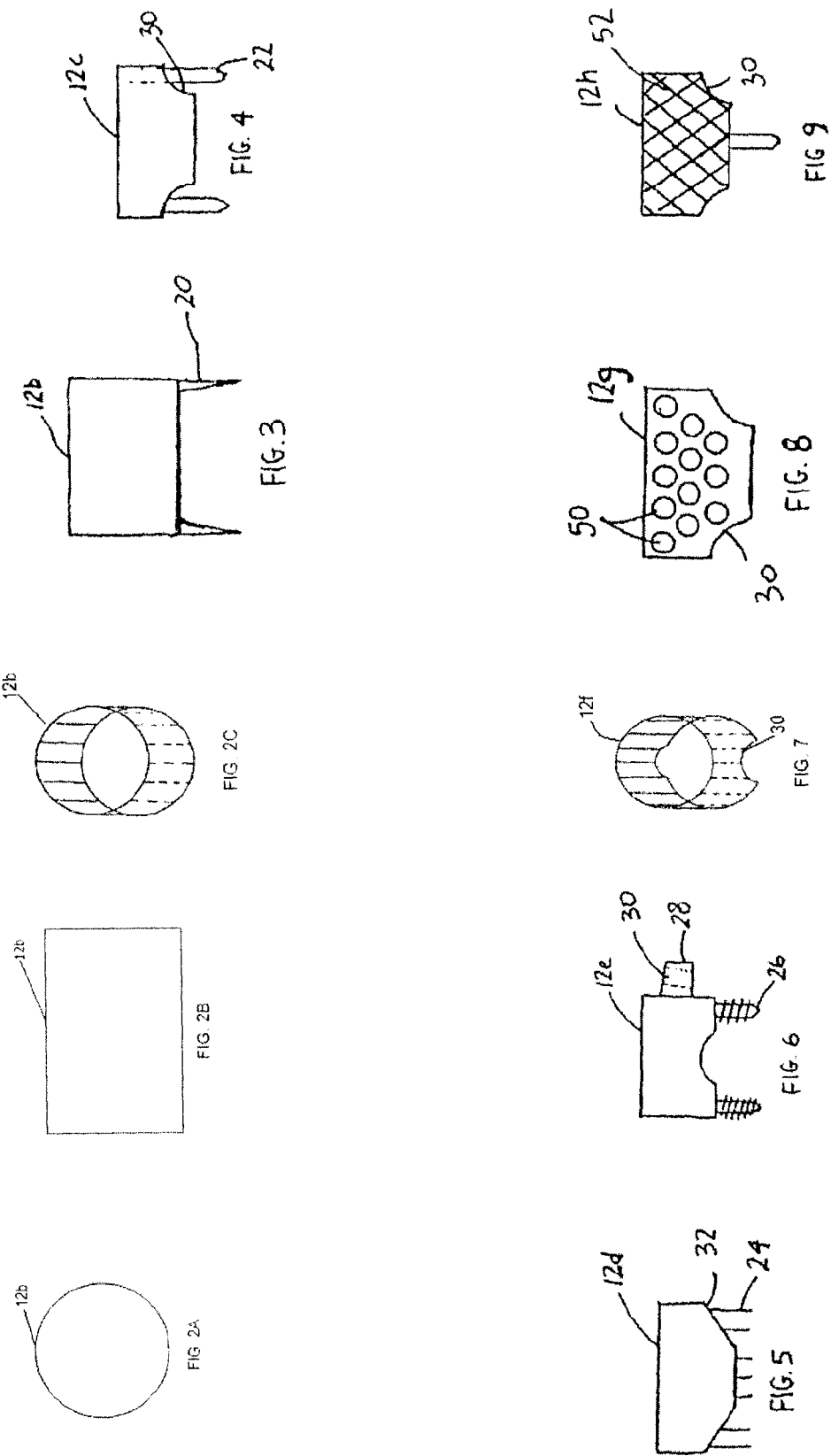

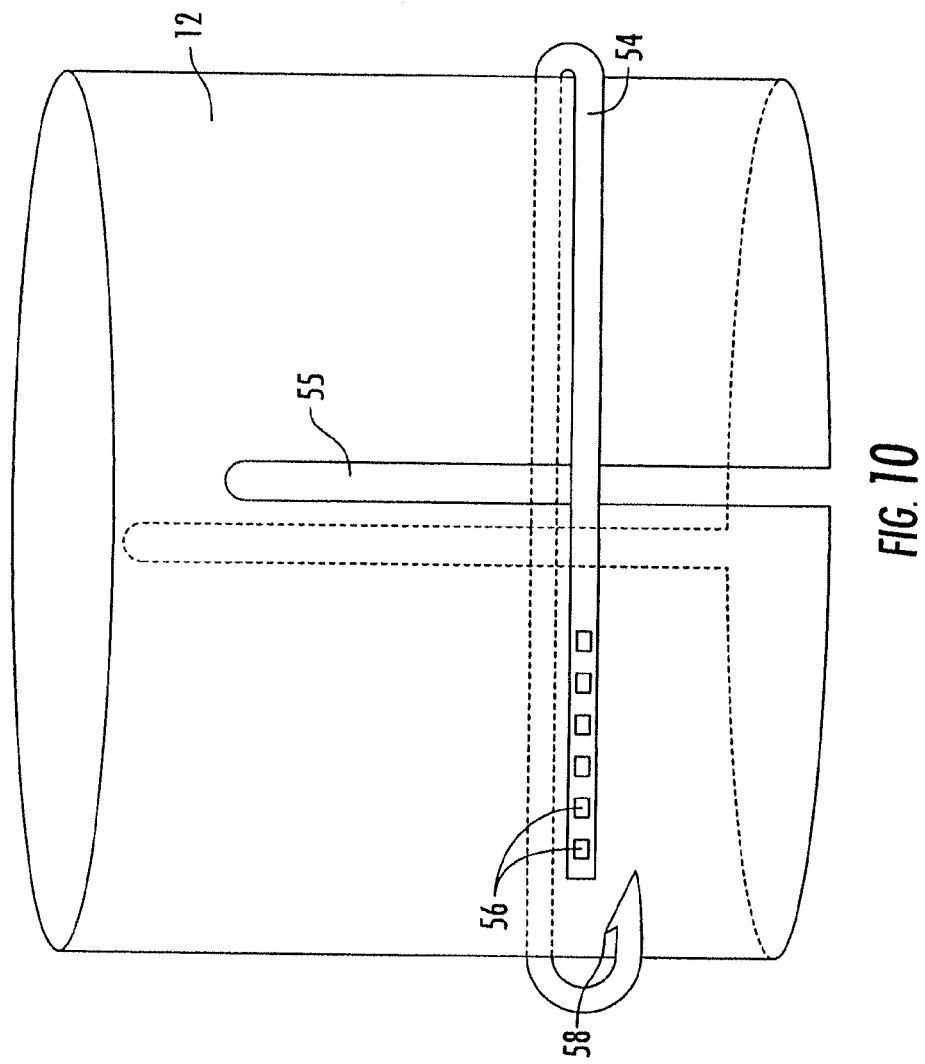

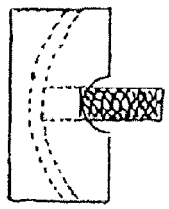
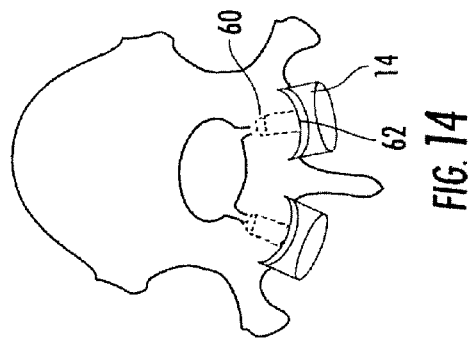
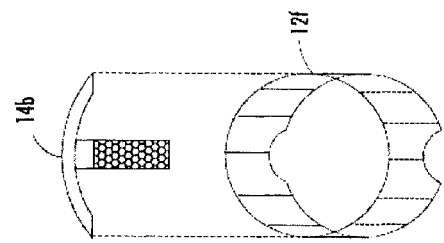
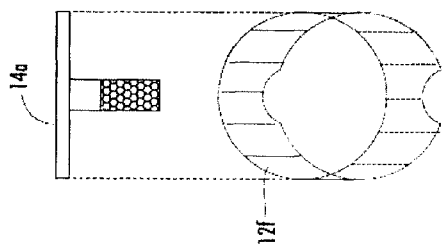
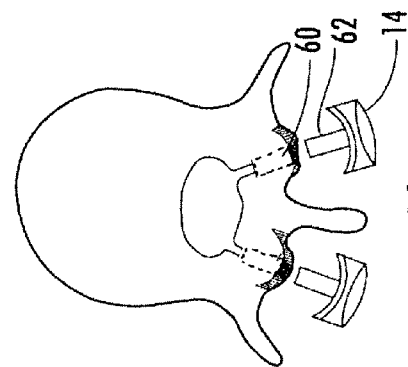

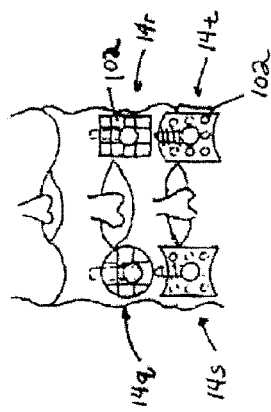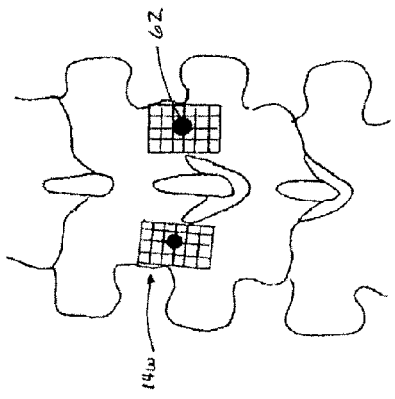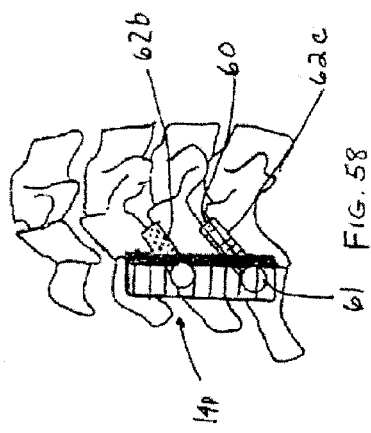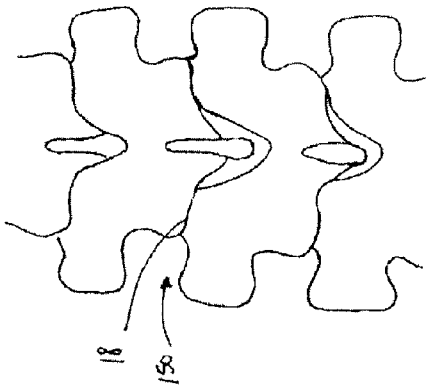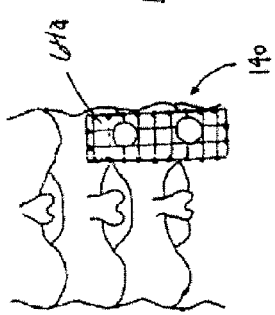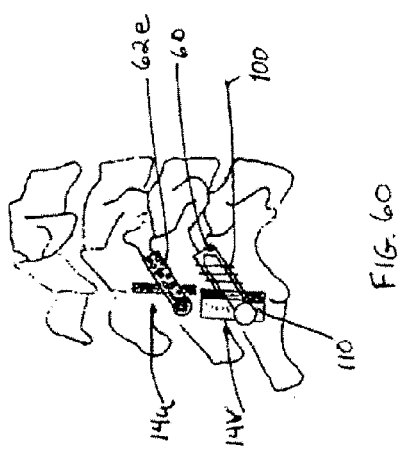

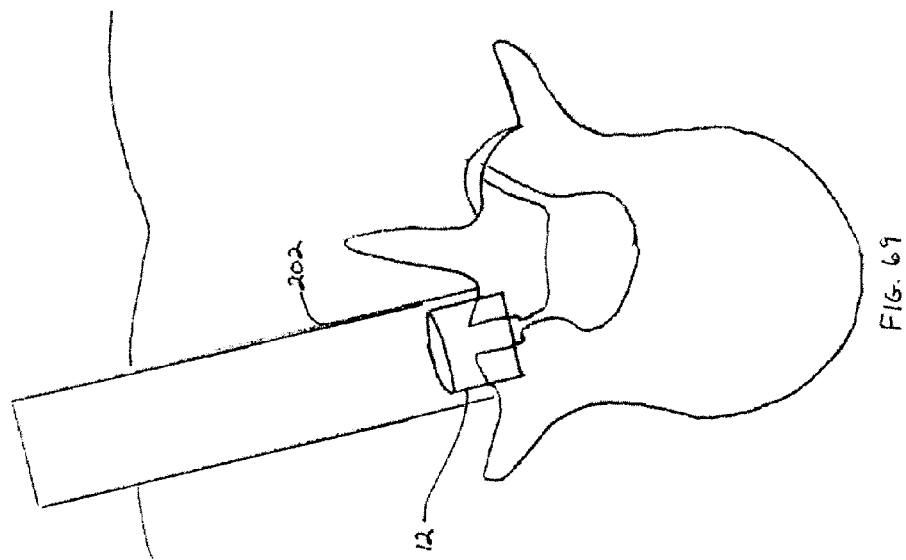
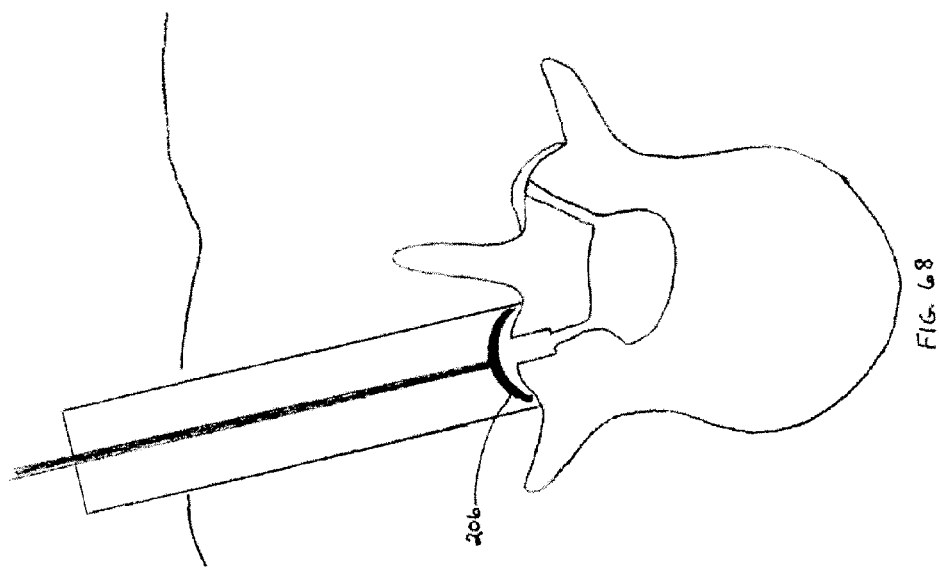

FACET JOINT FUSION DEVICE AND METHOD FOR USING SAME

This application claims the benefit of U.S. Provisional Patent Application Ser. No. 60/982,234, filed Oct. 24, 2007.

FIELD OF THE INVENTION

The invention relates to medical devices, and more particularly, to methods and systems for promoting stabilization and/or fusion of the facet joint of the spine.

BACKGROUND OF THE INVENTION

There are many reasons for back pain, which is estimated to occur in about 80% of the population at some point in their lifetime. The pain may originate from a number of different reasons or causes including, but not limited to, ligamentous/muscular injury to the paravertebral soft tissues, facet joint(s), disc internal derangement, compression of spinal nerves and instability of the spinal column. Conservative treatment usually helps ameliorate the discomfort. Life style modifications, rest, heat, cold therapy, anti-inflammatory medications, physical therapy, losing weight, conditioning the spinal musculature and abdominal muscles, therapeutic cortisone injections, etc. may help decrease the back discomfort. In some cases, however, back pain persists despite conservative treatment.

When conservative treatment fails to sufficiently reduce the patient's pain and improve the patient's quality of life, surgical correction of the spinal column may be performed. There are several types of procedures that may be performed in an attempt to alleviate back pain. For example, spinal decompression can be performed to relieve compression from spinal nerves that are being impinged by a protruding disc or boney/soft tissue overgrowth (lamina, facet, ligamentum flavum) into the spinal canal.

Another procedure is a fusion or arthrodesis of the spinal column. A fusion is sometimes utilized to stop the painful motion of the mobile section of the spinal column. Examples of where fusion may be utilized include where there is instability of the spinal segment (a disc and its adjoining vertebrae), pain from a degenerated and torn disc, or arthritic condition of the facet joint which may lead to pain.

A fusion is performed by preparing the boney surfaces of the adjoining vertebrae. Typically, the soft tissues (disc, cartilaginous intervertebral endplates, facet joint cartilage/capsule, and/or musculature from the transverse process/par articularis) are removed to expose the intended fusion area boney surfaces. Then, bone graft or other bone growth promoting substances are placed in the area of the intended fusion area (intervertebral disc space, interspinous process space, lateral gutter between the transverse process and/or in the facet joints).

Instrumentation of the spinal segment that is being fused is commonly performed to help immobilize that segment until a solid fusion occurs. Cages, screws, rods, plates and/or the like are used to immobilize the spinal segment until a solid fusion occurs.

Common instrumentation techniques include an interbody fusion with screws, cage(s) or plate fixation (PLIF—posterior lumbar interbody fusion; ALIF—anterior lumbar interbody fusion; XLIF extreme lateral interbody fusion), posterior pedicle instrumentation, transfacet pedicle screw fixation, interspinous process spacer, translaminar facet screw fixation and a combination of one of the above mentioned instrumentations. Each one of these spinal instrumentations has unique risks associated with their use. An ALIF has a potential risk of injuring an abdominal organ or a major vascular vessel, and/or causing retrograde ejaculation in males. An XLIF may injure a nerve root, lumbar plexus or sympathetic chain, major vascular vessels and/or abdominal organs. A PLIF has the risk of an epidural scar, nerve root injury, and/or dural tear. Posterior instrumentation usually entails inserting pedicle screws and connecting them to a rod or plate. Placement of the pedicle screws can be difficult and incorrect screw placement can cause nerve injury, an epidural tear or a vascular injury. Further, pedicle or facet screw placement usually requires large, invasive exposure to properly place the screws. Even minimally invasive exposure techniques require two moderately sized incisions in order to place the hardware.

Over 350,000 spinal fusions are currently done in the US yearly to alleviate spinal pain. With the increased age of the population, it is anticipated that complaints of degenerative problems of the spine will increase. Hence, spinal fusions and the need to stabilize the spine will become even more prevalent.

Two known products that are in the market for lumbar facet fusion are the TruFUSE allograft and a transfacet screw type of fixation. The TruFUSE allograft is a facet fusion allograft with a Mores taper that is placed into the facet joint. Allograft and/or autograft are typically placed into the facet joint to help induce a fusion across the joint.

There are many types of screws that have been used to perform a transfacet fixation. The technique in which it has been performed varies. A translaminar facet screw fixation, transfacet pedicle screw fixation and a pedicle screw fixation have been used to immobilize the facet joint. A Facet Fixation System has also been introduced by US SPINE to achieve a transfacet fixation.

The present invention is unique from these and all other spinal fusion devices in that it is based on an encircling device and/or top cap to immobilize the facet joint and which allows fusion of the facet joint. This invention would stabilize the facets in a matter that pedicle screws in two vertebral bodies would not be necessary. This fusion device and technique could be performed in a minimally invasive manner and potentially be performed as an outpatient procedure.

SUMMARY OF THE INVENTION

The present invention is an improvement over the prior methods and devices for facet joint fusion in the use of an encircling device and/or top cap that may be placed in a minimally invasive way (although it can also be performed through an open approach) that can potentially allow a fusion to occur as an outpatient procedure. The present invention would also permit stabilization of the facets in a manner such that pedicle screws in two vertebral bodies would not be necessary.

In particular, the methods, devices and systems of the present invention promote stabilization and fusion of the intervertebral facet joints. Additionally, an arthrodesis (fusion) of a facet joint via the device that is placed around the facet joint and/or into the facet joint and the adjacent subchondral facet joint bone is a less invasive manner to achieve an arthrodesis (fusion) of the spine as compared to pedicle screw fixation devices that are presently being used. The facet joint arthrodesis (fusion) potentially can be performed as an outpatient procedure and may be introduced via any manner including, but not limited to, an open surgical technique, a minimally invasive percutaneous technique, an endoscopic/arthroscopic approach and/or an imaging guidance technique. Associated risks of more invasive forms of fusion (e.g., complications from entering into an abdominal cavity to perform an anterior interboby fusion, bleeding, and retaining of large hardware devices) are therefore decreased. The technique may be done as a stand-alone procedure or in combination with currently available devices or techniques (anterior, interspinous process or posterior fusions) using pedicle screws, interspinous devices, and/or interbody spacers to enhance the potential of a spinal fusion.

The encircling device may take several forms including, but not limited to, a continuous cylindrical ring or a cylindrical ring with tangs to anchor the device. Different shapes including, but not limited to, round, elliptical, parallelogram or square may be used for the encircling device. A tightening/relaxing mechanism may also be used to adjust the size of the encircling device, or the encircling device may be a fixed size.

An attachment on the encircling device may be used to allow a screw or other fixation device to affix to a pedicle, pars articularis, spinous process, facet articular process, lamina or other spinal boney anatomy to give further fixation to the encircling device. The attached device may also affix to an adjacent spinal device such as a interspinous process spacer or other inserted spinal device for further fixation on the encircling device. It is appreciated that the encircling device may have varying levels of contact with the facet. For example, in use, there are some points of contact between the device and the facet articular processes. However, the device may or may not contact the outer perimeter of the facet joint. The encircling device may also, among other things, partially contact the facet, penetrate the facet without touching the external perimeter of the facet, or have portions that enter the pedicle, pars articularis, facet articular process, transverse process, spinous process and/or the lamina.

The encircling device may be made of a variety of different materials including, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK), or carbon filled PEEK. The encircling device also may be made of bioresorbable implant material or inert material. Amongst other things, the device may be made of radiolucent materials with or without some radiopaque makers to allow visualization of the implatable device. It may also be made of radiopaque material.

The encircling device may take different forms and may be made of any solid material. It is appreciated that the device may be made of, amongst other things, a semi-rigid material, a rigid material or an adjustable/expandable/compressible material. In other embodiments, it may be made of a memory shape material that reshapes itself when introduced to a catalyst. The device may also be custom made to the patient's particular anatomy, determined by existing or future radiographic modality.

The encircling device also may be coated with agents that promote or enhance bone growth, such as, but not limited to, bone morphogenic proteins, genetic components or hydroxyapatite.

It is further appreciated that the encircling device may also have a variety of surfaces. For example, the encircling device may be, among other things, perforated or otherwise have one or more open spaces to promote boney growth through the device itself. The surface also may be, but is not limited to, smooth, serrated, rough, porous, perforated, meshed, beaded, with protruding spikes, ridges, pegs, protrusions, screws or the like. Some of these structures also promote stabilization of the device on the facet joint and of the facet joint itself.

While the encircling device or top cap may be used independently, the encircling device and top cap may be used together to facilitate or promote fusion of the facet joint. The top cap may have an intra-articular insert, which may have bone growth promoting properties, and/or a screw which enhances stabilization of the encircling device and/or the top cap directly or indirectly. It is also appreciated that the insert and/or screw may be extra-articular.

When used with the encircling device, the top cap may be, among other things, placed through the top of the encircling device and submerged into the encircling device or placed over or partially through the top cap. It is also appreciated that the top cap may be placed first and then the encircling device may be placed around and/or partially through the top cap. It is further appreciated that the encircling device and top cap may be integrally formed.

The top cap serves the purposes of, among other things, (a) retaining bone-growth agents (bone morphogenic proteins, bone growth promoting materials, bone graft, bone allograft, bone material of any form, genetic components, bone adhesive, etc.) within and around the facet joint; (b) promoting internal fixation of the facet joint and (c) promoting bone growth/fusion itself, as the top cap (1) acts to immobilize the facet joint; (2) may be of an embodiment which promotes boney growth through the top cap; and/or (3) may be coated with agents that promote or enhance bone growth, such as bone morphogenic proteins, genetic components, hydroxyapatite, etc. The area above the top cap, and within the encircling device, may be used as a container to place fusion promoting substances. In another embodiment, the top cap is not submerged into the encircling device, but instead covers the encircling device from the outside.

In order to promote or enhance boney growth into the device, the surface of the top cap may be, among other things, serrated, rough, porous, perforated, meshed, textured, beaded, with protruding spikes, with ridges or and/or coated with agents that promote or enhance bone growth. Other embodiments of the top cap may utilize one or more fasteners or fixation devices such as, but not limited to, screws, pegs, tangs or plugs to create fixation with the surrounding bone or other spinal implants.

The top cap may be of a variety of different shapes and configurations including, but not limited to: a tack shape with a shaft to be inserted into the facet joint and a perpendicular top; or just a top member. The shaft of the top cap may be screwed, tapered interference-type fitted, impacted or secured by other known ways in the art into the facet joint and/or surrounding bone.

If not self-affixing, the top cap can be locked or affixed to the facet joint or the encircling device to prevent disengagement in a variety of known ways including, but not limited to, using pins, levers, wedges, spring members, spikes, screws or pegs, or by tightening the encircling device. The top cap and the encircling device also may be made of similar or different materials which may, among other things, melt together, affix together, interdigitate together, cut into each other or the like causing fixation between the structures. When used with an encircling device, the fixation device may be either internal or external to the encircling device.

Additional fixation of the encircling device and/or the top cap may be achieved by an anchoring device or attachment member inserted into a pedicle, pars interarticularis, spinous process, interspinous process spacer, facet articular process, transverse process, lamina, sacral ala or other spinal bony anatomy and affixed to the encircling device and/or the top cap. The anchoring device or attachment member may be a screw, peg, plug, spikes, tang or the like that is affixed to the bone and the encircling device, and/or the top cap, through a connector on the device. In order to obtain more bone purchase, it is also appreciated that the anchoring device may be expandable.

One anchoring embodiment is a pedicle anchoring fixation wherein a screw may be placed into the pedicle adjacent to the ipsilateral facet joint that is being fused. This screw is attached to the encircling device and/or the top cap through a connector that may adjust (e.g., swivel, pivot, elongate or shorten) to accommodate the desired position of the anchoring screw. Once the connector is in the desired location in relation to the encircling device and/or top cap and the screw, it can be fixed in this position through a tightening mechanism or the like. The connector, which is attached to the encircling device and/or the top cap, may also be fixed allowing only a certain entry of an anchoring screw. Overall, the anchoring fixation allows additional fixation of the encircling device and/or the top cap relative to the facet joint.

The encircling device, top cap, interspinous process spacer and anchoring device may be made of a variety of different materials including, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK), or carbon filled PEEK. The device may be made of bioresorbable implant material or inert material. Amongst other things, the device may be made of radiolucent materials with or without some radiopaque makers to allow visualization of the implatable device. It may also be made of radiopaque material. It is appreciated that the encircling device, top cap, interspinous process spacer and anchoring device may be made of the same material and textures or may be made of different materials and/or textures.

The encircling device, top cap, interspinous process spacer and anchoring device may take different forms and may be made of any solid material. The embodiment may be made of, amongst other things, a semi-rigid material, a rigid material, an adjustable/expandable/compressible material or combinations thereto. In other embodiments, it may be made of a memory shape material that reshapes itself when introduced to a catalyst. The device may also be custom made to the patient's particular anatomy, determined by existing or future radiographic modality.

The encircling device, top cap, interspinous process spacer and anchoring device also may be coated with agents that promote or enhance bone growth, such as, but not limited to, bone morphogenic proteins, genetic components or hydroxyapatite. In order to promote or enhance boney growth into the device, the surface of the device(s) may be, among other things, serrated, rough, porous, perforated, meshed, textured, beaded, with protruding spikes, with ridges or and/or coated with agents that promote or enhance bone growth.

It is therefore an object of the present invention to provide a new device and method for arthrodesis of cervical, thoracic and/or lumbar facet joints.

Another object of the present invention is to provide a new device and method for arthrodesis of a facet joint that is safer and less invasive.

It is still yet another object of the present invention to provide a new device and method for arthrodesis of a facet joint that may be done on an outpatient basis.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 2A is a top plan view of one embodiment of an encircling device of the present invention.

FIG. 2B is an elevated side view of the encircling device of FIG. 2A.

FIG. 2C is a perspective view of another embodiment of an encircling device of the present invention.

FIG. 3 is an elevated side view of an encircling device with two tangs extending down from bottom side of the device.

FIG. 4 is an elevated side view of an encircling device with two pegs extending from the bottom side of the device.

FIG. 5 is an elevated side view of an encircling device with multiple spikes extending from the bottom side of the device.

FIG. 6 is an elevated side view of an encircling device with screws placed through the bottom of the device for additional stabilization and a connector with a channel on the side to introduce a screw, peg or other stabilizing device for addition stabilization of the encircling device.

FIG. 7 is a perspective view of an encircling device having arcuate carved-out areas on its bottom.

FIG. 8 is an elevated side view of a perforated encircling device with varying depth.

FIG. 9 is an elevated side view of another embodiment of an encircling device with a mesh surface and two superimposed pegs for enhanced stabilization of the device.

FIG. 10 is a perspective view of an encircling device with a tightening band extending about its outer circumference.

FIG. 11A is an exploded view of a top cap and an encircling device wherein the top cap has different textures, namely small fine pores in the cap portion and larger pores for boney ingrowth in the shaft.

FIG. 11B is an elevated side view of the top cap inside the encircling device of FIG. 11A.

FIG. 12A is an exploded view of another embodiment of a top cap and an encircling device wherein the top cap has different textures, namely small fine pores in the cap portion and a mesh-like texture for boney ingrowth in the shaft.

FIG. 12B is an elevated side view of the top cap inside the encircling device of FIG. 12A.

FIG. 13 is a top plan view of a vertebra showing a pair of holes reamed through the facet joint for a pair of top caps, and wherein the peripheral and lateral facet articular process has been decorticated to expose bleeding cancellous bone which will contact the undersurface of the top cap as it is fully inserted into the facet joint.

FIG. 14 is a top plan view of a vertebra with the top caps placed into the reamed facet joints.

FIG. 57 is a partial elevated view of a cervical spine with a top cap placed over lateral masses, wherein two central shafts have been placed through the top cap and into two facet joints.

FIG. 58 is a partial side elevated view of a cervical spine with the top cap, with a dorsal container, resting on the lateral masses. The central shafts are inside the decorticated and reamed facet joints and are of different configuration, namely, beaded and textured with ridges.

FIG. 59 is a partial elevated view of a cervical spine showing a plurality of top caps having different top configurations and different shafts.

FIG. 60 is a partial elevated side view of a cervical spine with two top caps in the facet joints, wherein the upper top cap has a porous central shaft and the lower top cap has a dorsal container that is perforated and a central screw which is screwed into the facet joint.

FIG. 61 is a partial elevated side view of a thoracic spine.

FIG. 62 is partial elevated side view of the thoracic spine of FIG. 61 having two perforated top caps on top of a facet joint and with the central shaft in the facet joints.

FIG. 68 is a top plan view of a vertebra illustrating the step of measuring the facet.

FIG. 69 is a top plan view of a vertebra illustrating an encircling device being placed around or in the facet joint.

DETAILED DESCRIPTION OF THE INVENTION

Figure 1A:
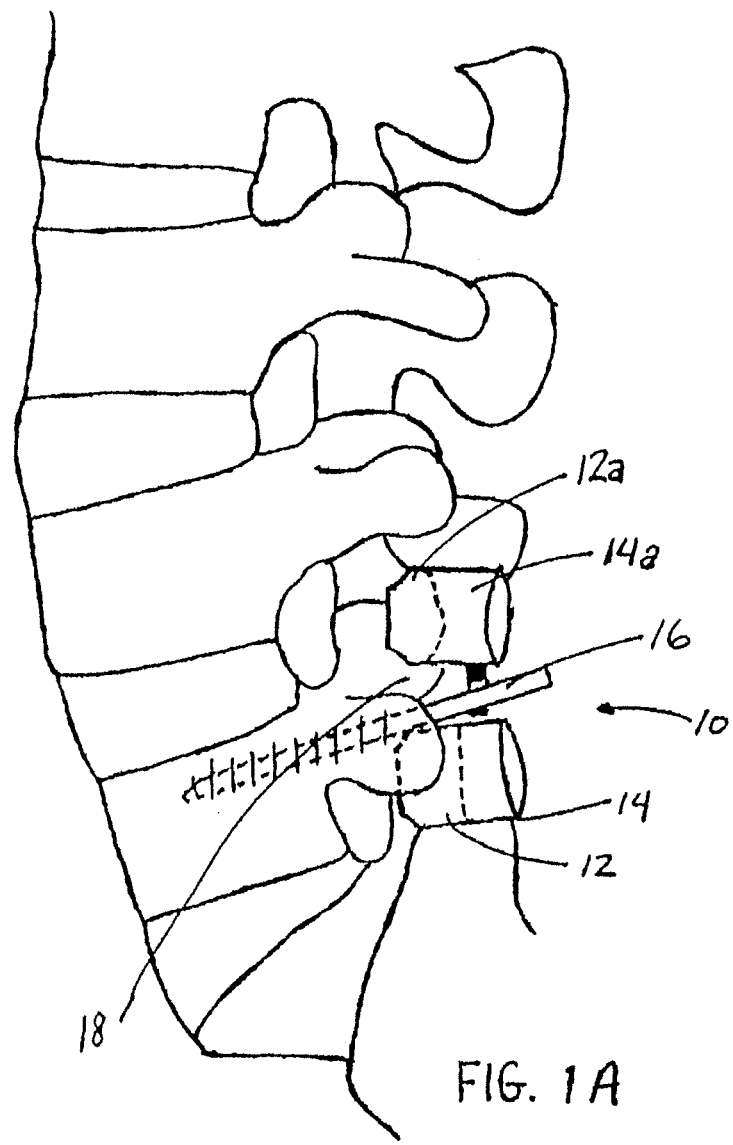
FIG. 1A is a partial elevated side view of a lumbar spine with two encircling devices, top caps and an anchoring screw.

While this invention is susceptible of embodiment in many different forms, there is shown in the drawings and will herein be described in detail several specific embodiments, with the understanding that the present disclosure is to be considered merely an exemplification of the principles of the invention and the application is limited only to the appended claims.

Figure 1B:
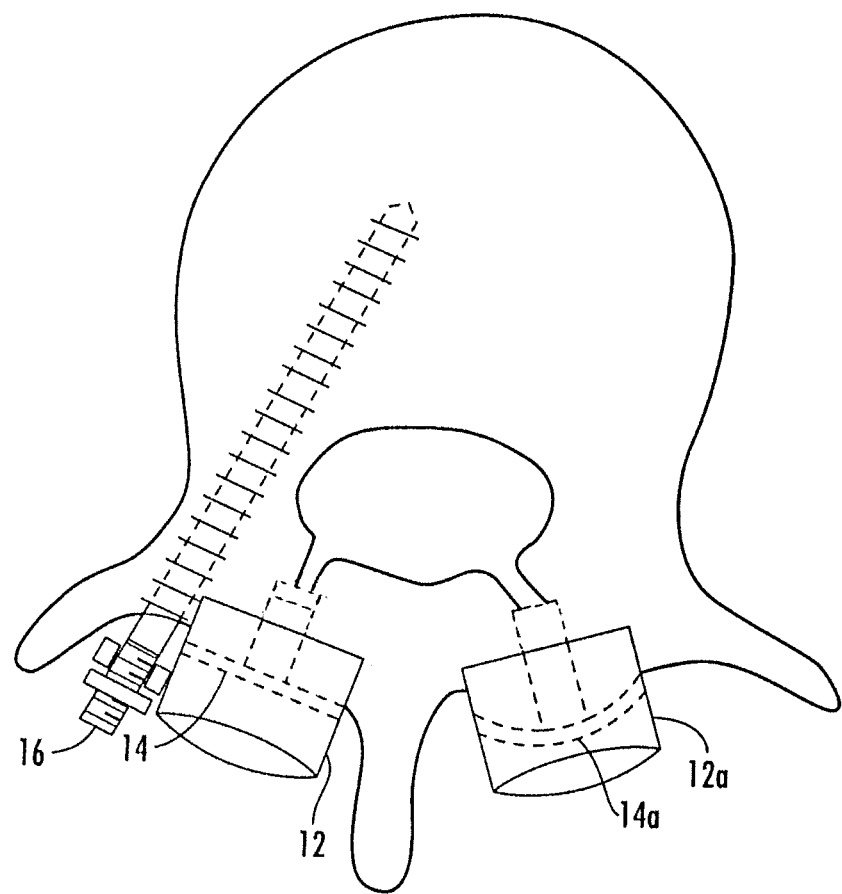
FIG. 1B is a is a top plan view of a vertebra with two encircling devices placed around the facet joints and two corresponding top caps being driven into the pre-reamed facet joints, wherein one encircling device has an anchoring screw which has been placed through the connector of the encircling device and into the pedicle/vertebral body.

Referring to the drawings, several embodiments of the facet joint fusion device and its components are shown. The facet joint fusion device, generally designated by the numeral 10, may include one or more of the following: an encircling device 12, a top cap 14 and an anchor or attachment member 16. In application, one or more facet joint fusion devices may be inserted around and/or within a facet joint 18 (cervical, thoracic or lumbar) to immobilize the joint in order to achieve an arthrodesis (fusion) of the joint. Examples of a pair of facet joint fusion devices 12, 12a applied to a lumber spine 20 and vertebrae are illustrated in FIGS. 1A and 1B.

The encircling device may take several forms to inhibit facet joint motion, as exemplified in the figures. Referring now to FIGS. 2A through 2C, embodiments of the encircling device 12b are shown as a continuous cylindrical ring. In operation, the device may or may not contact the outer perimeter of the facet joint 18. It is appreciated that there are some points of contact between the device and the facet articular processes and there may be partial contact of the facet by the device. For example, the encircling device may have a wall within the encircling device that rests on the facet articular process or facet joint. The encircling device also may penetrate the facet without touching the external perimeter of the facet and may have portions which enter the pedicle, pars articularis, facet articular process, transverse process, spinous process, sacral ala and/or the lamina.

The encircling device may include one or more fixation devices to facilitate fixation to the facet. As shown in FIG. 3, one or more tangs 20 may extend from the bottom of the encircling device 12b to capture more boney surface and to assist in fixing or anchoring the encircling device 12b relative to the facet joint 18. This increases the stability of the internal fixation. Referring now to FIGS. 4 through 6, the encircling device 12c, 12d, 12e may also have one or more pegs 22, spikes 24, or screws 26 in place of, or in addition to, the tangs 20. It is appreciated that the pegs, spikes and screws may be attached to the encircling device in any of the known ways. It is further appreciated that the encircling device may include a connector 28 extending partially inward or outward and having a hole 30 sized to accept the body of a fixation device such as, but not limited to, a peg, spike, hook or screw. The accepting fixation device may be secured to the connector via a friction apparatus such as a nut. There may also be an attachment for a connection to a screw or other fixation device that affixes to a pedicle, pars interarticularis, spinous process, transverse process, facet articular process, lamina, sacral ala, intraspinous process spacer or other spinal boney anatomy to give further fixation to the encircling device. It is also appreciated that the spikes and pegs may be fixed to the encircling device in a known way such that the ends of the fastening member extend beyond the bottom of the encircling device. The attachment may be of any known fastening member that attaches a device to bone and or other separate embodiments.

The encircling device may also have carved-out areas on the bottom side of the device to permit the non-carved out areas to sit deeper into the facet articular process. For example, referring to FIGS. 4 through 9, the encircling device 12c, 12d, 12e, 12f, 12g, 12h may have two arcuate, angled or straight carved out areas 30, 32 on the bottom side of the device. In use, the deepest part of the carved-out area sits on the pars articularis above and below the facet joint or at the proximal and distal ends of the facet joint.

Referring now to FIG. 8, the encircling device 12g may be perforated or otherwise have one or more open spaces 50 to promote boney growth through the device 12g itself and enhance fixation of the encircling device 12g relative to the facet joint 18. As shown in FIG. 9, the encircling device may also have a meshed surface 52 to promote boney growth. In addition to being perforated or meshed, it is appreciated that the surface of the encircling device 12 may also be, among other things, smooth, serrated, rough, porous, textured, beaded, or of a matrix configuration, and/or include protruding spikes, ridges, pegs, protrusions, screws or the like. Some of these structures also promote stabilization of the device on the facet joint and of the facet joint itself.

While a number of shapes and forms for the encircling device are shown and disclosed, it is appreciated that the encircling device may be of other shapes and forms, including but not limited to, elliptical, oblong, parallelogram and rectangular, and not depart from the scope of the present invention. The encircling device may be a continuous encircling device or partly or completely slotted. It is also appreciated that the device may be a fixed size, or may vary in size by means of a known tightening/relaxing mechanism such as, but not limited to a ratcheted device with a peg that may sequentially moved, a pliant or memory-shape material.

Referring now to FIG. 10, one embodiment of a tightening/relaxing mechanism is shown as having a band 54 extending around the outer circumference of an encircling device 12 having a pair of slots 55 extending vertically therein to permit the encircling device to be tightened or compressed. One end of the band 54 includes a plurality of slots or openings 56 that are sized to accept a peg or protruding member 58 proximate the other end of the band. In operation, once the encircling device is squeezed by tightening the band or through other means, the peg is inserted into the corresponding slot to maintain the tightened position of the encircling device.

The encircling device may be made of any solid material including, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK), or carbon filled PEEK. It may be made of, among other things, a semi-rigid or rigid material. In other embodiments, it may be made of, among other things: a memory shape material that reshapes itself when introduced to a catalyst; a bioresorbable implantable material; an inert material; radiolucent materials with or without some radiopaque markers to allow visualization of the implantable device; or a radiopaque material. The device may also be custom made to the patient's particular anatomy, determined by existing or future radiographic modality. The encircling device also may be coated with agents that promote or enhance bone growth, such as, but not limited to, bone morphogenic proteins, genetic components or hydroxyapatite.

Referring to FIGS. 11A, 11B, 12A and 12B, a top cap 14a, 14b may be used with the encircling device 12f, to enhance fixation, and thus fusion, of the facet joint 18. It is also appreciated that the top cap may be used without the encircling device. In use, as shown in FIGS. 13 and 14, the top cap 14 is placed on the dorsal aspect of the joint. Accordingly, prior to use of the top cap, appropriate reaming of the facet joint may be done to create a hole 60 that corresponds with the central shaft or central member 62 of the top cap 14. A firm fit between the central shaft 62 and the hole 60 should be established to prevent movement of the top cap 14 relative to the facet joint 18. It is also appreciated that further decortications of a portion of the facet joint/articular process surface may also be performed to place bone growth promoting or enhancing substance within the facet joint in order to increase the surface of area that a fusion can occur in the facet joint. Some of the dorsal aspect and peripheral of the facet articular process may also be shaved off to improve contact of the underside of the top of the top cap with the decorticated facet articular process. The top cap can then be placed into the decorticated and reamed facet joint/articular process. While a central shaft or member is shown, it is appreciated that the top cap may include one or more members extending from the central portion of the top cap and/or around the periphery of the bottom of the top cap.

In practice, the top cap 14 may be placed through the top of the encircling device 12 and submerged into the encircling device 12. The top cap 14 may also be placed initially on the facet joint 18 and then the encircling device 12 may be inserted over or partially through the top cap 14. Screw fixation may also be used to enhance fixation of the encircling device 12 and/or the top cap 14. Referring to the figures, when placing a screw 86, or the like, into the facet articular process while being perpendicular to the facet joint line and adjacent to the inner aspect of the encircling device, the facet articular process may be pushed away from the encircling device, thereby clamping the facet joint. Net result of this embodiment is that the central shaft will have a tighter fit on the facet joint. In other embodiments, the top cap is not submerged into the encircling device but instead covers the encircling device from the outside.

It is further appreciated that the top or top cap may be integral with the encircling device. In one embodiment, the encircling device may include an attached or integral cross-sectional wall extending in its interior with or without an anchoring device/attachment member. The cross-sectional wall may have one or more perforations to promote bone growth through the device.

The top cap serves the purposes of, among other things, (a) retaining bone-growth agents (bone morphogenic proteins, bone growth promoting materials, bone graft, bone allograft, bone material of any form, genetic components, bone adhesive, etc.) within and around the facet joint; and (b) promoting bone growth/fusion itself, as the top cap (1) act to immobilize the facet joint; and/or (2) may be coated with agents that promote or enhance bone growth, such as, but not limited to, bone morphogenic proteins, genetic components, hydroxyapatite. Furthermore, the area of the encircling device above the top of the top cap, but within the encircling device, may be used to place bone graft or other bone growth promoting or enhancing substances therein. It is also appreciated that bone growth promoting or enhancing substances may be used within the encircling device itself. When the top cap that has a dorsal container is used without an encircling device, the dorsal container may be used to place bone graft or other bone growth promoting or enhancing substances therein. Some of the growth promoting/enhancing substances include, but are not limited to, osteogenic substances, osteo-conductive and/or osteo-inductive substances that are naturally occurring or artificially made, bone in any of its forms, hydroxyapetite, calcium phosphate compounds, genetic material coding for bone production, bone morphogenic proteins, and other as yet undiscovered bone forming agents.

The top cap 14 generally includes a top 64 and one or more members extending downward therefrom. While the top 64 of the top cap 14 may be flat or arcuate, it is appreciated that it may be rounded or of any variety of different configurations and not depart from the scope of the present invention.

Figure 15A:
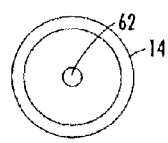
FIG. 15A is a bottom plan view of one embodiment of a top cap with a central peg that can be placed into the facet joint.
Figure 16:
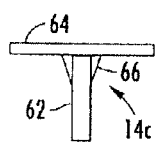
FIG. 16 is an elevated side view of a top cap with a flat top and flanges on the central shaft.
Figure 17:
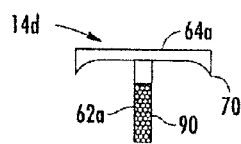
FIG. 17 is an elevated side view of a top cap having protruding surfaces extending downward from the top and a meshed central shaft.
Figure 15B:
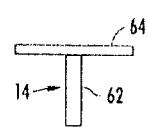
FIG. 15B is an elevated side view of the top cap of FIG. 15A.
Figure 18:
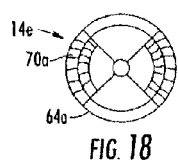
FIG. 18 is a top plan view of a top cap having a pair of flanges extending downward from the top.
Figure 19:
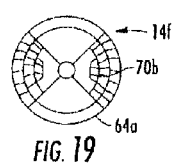
FIG. 19 is a top plan view of a top cap having a pair of tapered flanges extending downward from the top.

The top cap may take several forms to enhance fixation and fusion of the facet joint and may include one or more top cap fixation devices to facilitate attachment to the encircling device and/or facet. Referring now to FIGS. 15A and 15B, one embodiment of a top cap 14 is shown having a flat top 64 and a central shaft 62. The top cap may also be just the top without a shaft. As shown in FIG. 16, the top cap 14c may include one or more flanges 66 extending from the top 64 to the central shaft 62 to provide for additional fixation of the top cap 14 to the facet joint 18. Referring now to FIGS. 17 through 19, the top 64 of the top cap 14d, 14e, 14f may also include protruding surfaces such as, but not limited to, flanges 70, 70a, 70b that extend downward from the top 64 to enhance boney contact and increase stability of the top cap 14d, 14e, 14f on the facet joint 18. It is appreciated, as shown in FIGS. 18 and 19, that the top cap may include open areas to permit boney growth through the top cap for additional stabilization. Referring now to FIG. 19, the flanges 70b may be tapered inwardly toward the bottom.

Figure 20:
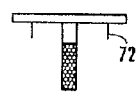
FIG. 20 is an elevated side view of a top cap having a pair of spikes extending downward from the top and a porous central shaft.
Figure 21:
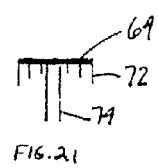
FIG. 21 is an elevated side view of a top cap having a plurality of spikes extending downward from the top and a pair of flanges in the middle.
Figure 22A:
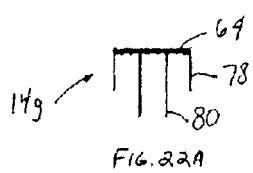
FIG. 22A is an elevated side view of a top cap with four pegs of varying lengths.
Figure 22B:
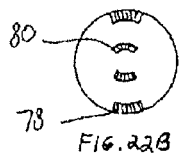
FIG. 22B is a bottom plan view of a top cap with four flanges.
Figure 23:
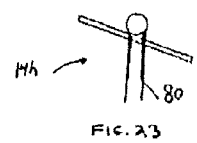
FIG. 23 is an elevated side view of a top cap with a central stabilizer consisting of two tangs which are placed into the facet joint.
Figure 40:
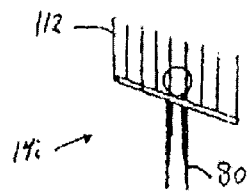
FIG. 40 is an elevated side view of a top cap that has a container made of vertical prongs.

It is appreciated that other types of protruding structures may be used to extend from the top 64 of the top cap 14. For example, as shown in FIGS. 20 and 21, one or more spikes 72 may extend from the bottom of the top 64. It is also appreciated, as shown in FIG. 21 that flanges 74 may be used in place of the central shaft 62 for placing into the decorticated facet joint 18. Referring now to FIGS. 22A and 22B, tangs 78 may be used toward the periphery of the top of the top cap 14g to enhance boney contact and increase stability of the top cap 14 on the facet joint. Additionally, as shown in FIGS. 23 and 40, tangs 80 may extend from the top 64 of the top cap 14h, 14i downward instead of a central shaft, screw or flange for inserting into the hole 60 in the facet joint 18. Bone growth promoter materials may be placed within the tangs 80. Instead of a solid central shaft, or the like, a liquid or non-solid substance which forms into a hard substance may be used. Examples of such transforming agent include, but are not limited to, calcium phosphate cement, silicate substituted calcium phosphate and polymethyl methacrylate.

Figure 22C:
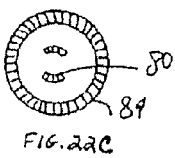
FIG. 22C is a bottom plan view of a top cap with a circumferential, peripheral flange and two flanges in the middle of the top cap.

Referring now to FIG. 22C, it is also appreciated that a circumferential flange 84 may be used around the periphery of the underside of the top of the top cap.

Figure 24A:
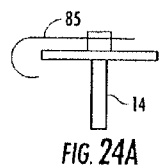
FIG. 24A is an elevated side view of a top cap with a hook extending through a connector on the top part of the central member.
Figure 24B:
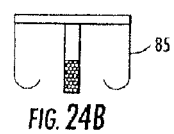
FIG. 24B is an elevated side view of a top cap with a pair of hooks extending down from the bottom side of the top cap.
Figure 24C:
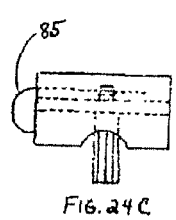
FIG. 24C is a side elevated view of an encircling device with a top cap and a hook extending through a connector on the top part of the central member of the top cap.
Figure 24D:
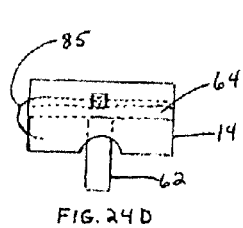
FIG. 24D is a side elevated view of an encircling device with a top cap and a hook extending through the top part of the central member of the top cap with the hook having been centrally pulled to lock the top cap in place.

As shown in FIGS. 24A through 24D, it is appreciated that one or more hooks 85 or bendable members may be used to affix the top cap 12 relative to the facet joint 18. Referring to FIG. 24A, the hook may extend through an opening in the top portion of or otherwise be attached to the central member through a connector. When the hook extends to the side, it is appreciated that the wall of the encircling device includes a corresponding slot to permit the hook to pass therethrough when the top cap is inserted into the encircling device as shown in FIG. 24C. As shown in FIG. 24D, once the top cap is inserted into the encircling device the hook may be pulled centrally and locked in position by the connector to retain the top cap in position. Referring to FIG. 24B, one or more hooks 85 may extend downward from the bottom of the top of the top cap.

Figure 25:
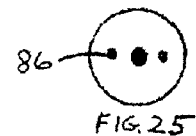
FIG. 25 is a bottom plan view of a top cap having a pair of screws and a central shaft.
Figure 27:
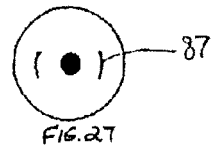
FIG. 27 is a bottom plan view of a top cap having a pair of flanges and a central shaft.
Figure 28:
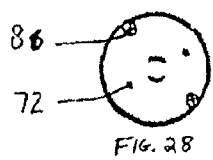
FIG. 28 is a bottom plan view of a top cap having two screws, two flanges and two pegs.
Figure 29:
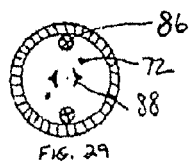
FIG. 29 is a bottom plan view of a top cap having a circumferential flange on the periphery of the top and a combination of two screws and two spikes that are placed through the top cap into the underlining boney structures and a pair of central spiked flanges that are to be placed into the facet joint.

Examples of other types of protruding structures that may be used to engage the bone include, but are not limited to, screws 86 (FIG. 25) or flanges 87 (FIG. 27). It is also appreciated that a combination of protruding structures may be used. Exemplary combinations of structures include, but are not limited to, a pair of screws 86 and pegs 72 (FIG. 28), or a pair of screws 86, a pair of pegs 72, a pair of spiked flanges 88 for engaging the hole in the facet joint, and a circumferential flange 84 (FIGS. 22 and 29)

Figure 26A:
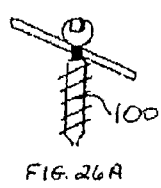
FIG. 26A is an elevated side view of a top cap having a screw.
Figure 26B:
FIG. 26B is an elevated side view of another top cap having a screw and a dorsal container.
Figure 30:
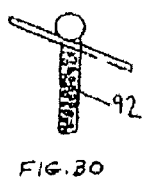
FIG. 30 is an elevated side view of a top cap embodiment with a porous central shaft.
Figure 31:
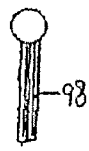
FIG. 31 is an elevated side view of a ridged central shaft.
Figure 32:
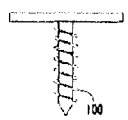
FIG. 32 is an elevated side view of a top cap with a flat top and a central screw.

Referring again to FIG. 17, the central shaft 62a may also have a meshed surface 90 around part of its length to permit bone promoting substances to be placed therein to promote bone growth. Alternatively, the central shaft 62 may also have perforations 92 (FIGS. 20 and 30) for promoting bone growth. The surface of the shaft 62 also may be serrated, rough, porous, beaded, textured, beaded, or have protruding spikes, ridges 98 (FIG. 31) or the like to promote or enhance boney growth into the device. As shown in FIGS. 26A, 26B and 32, it is also appreciated that a screw 100 may be used instead of a central shaft for engaging the hole 60 of the facet joint 18. While a central shaft or other structure is shown for engaging a hole in the facet joint, it is appreciated that the top cap may be used without a central engaging structure and not depart from the scope of the present invention.

Figure 33:
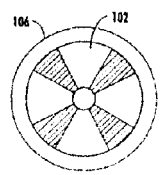
FIG. 33 is a bottom plan view of a top cap having open areas.
Figure 34:
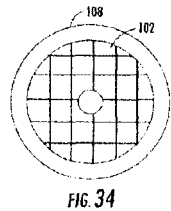
FIG. 34 is a bottom plan view of a top cap with a grid type top.
Figure 35:
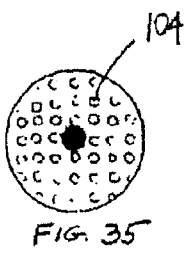
FIG. 35 is a bottom plan view of a top cap having a perforated top.

The top 64 also may be serrated, rough, porous, beaded, textured, perforated, meshed, textured or have protruding spikes, ridges or the like to promote or enhance boney growth into the device. As shown in FIGS. 33-35, it is also appreciated that the top 64 may have one or more open areas 102 or holes 104 for promoting boney ingrowth. The openings may be formed from structure having any configuration including, but not limited to, a plurality of flanges 106 or a plurality of intersecting pieces 108 that form a grid.

Figure 36:
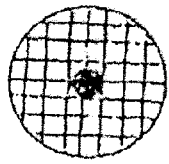
FIG. 36 is a bottom plan view of another top cap embodiment having a round top and a grid type top.
Figure 37:
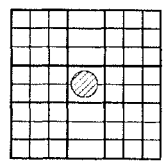
FIG. 37 is a bottom plan view of another top cap embodiment having a square top and a grid type top.
Figure 38:
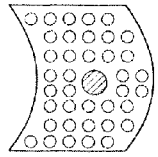
FIG. 38 is a bottom plan view of another top cap embodiment having a perforated top with a pair of curved sides, wherein one side of the top cap is concave and the other is convex.

While a number of different shapes are shown and disclosed, it is appreciated that the top cap may be of other shapes and forms including, but not limited to, tops that are round (FIG. 36), elliptical, parallelogram, rectangular and square (FIG. 37) or that have curved sides (FIG. 38), and not depart from the scope of the invention. The surface of the top may be flat (top 14a from FIG. 11A), curved, arcuate, dome shaped (top from FIG. 12A) or of any configuration. The top cap may be made of any material that is solid (rigid, semi-rigid) such as, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK) or carbon filled PEEK. The top cap also may be made of bioresorbable implantable material, or radiolucent material with or without some radiopaque markers to allow visualization of the implantable. As described herein, the top cap may also be made of material which promotes or enhances bone growth into or around the device such as material having a porous, serrated or textured interface. As shown in FIGS. 10A and 11A, it is further appreciated that the top cap may have textures, for example, small fine pores in the cap portion and larger pores or a mesh-like structure for boney ingrowth in the shaft.

Figure 39:
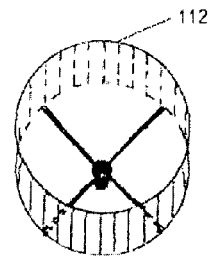
FIG. 39 is a perspective view of a top cap that has a container above the top.
Figure 41:
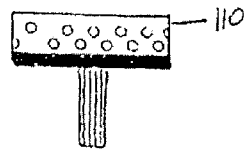
FIG. 41 is an elevated side view of a top cap with a container that has perforations and a ridged shaft.
Figure 42:
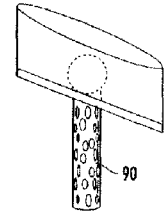
FIG. 42 is an elevated side view of another embodiment of a top cap with a dorsal container and a porous shaft.
Figure 43A:
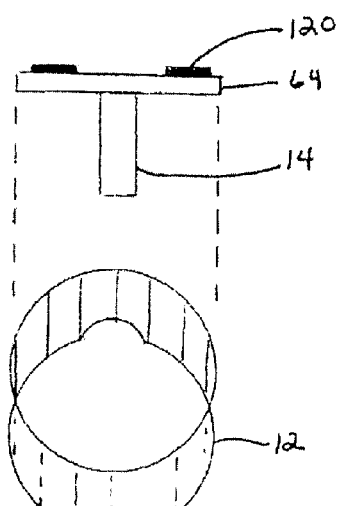
FIG. 43A is a partially exploded perspective view showing an encircling device and a top cap having a pair of pegs on its top for fixing the top cap within the encircling device.
Figure 43B:
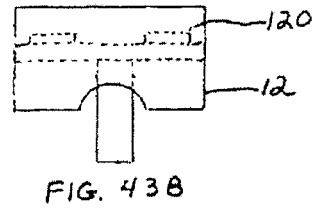
FIG. 43B is a side elevated view of the encircling device of FIG. 43A with the top cap inserted therein and the pegs in the disengaged position.
Figure 43C:
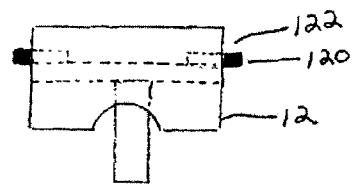
FIG. 43C is a side elevated view of the encircling device of FIG. 43A with the top cap inserted therein and the pegs in the engaged position with corresponding slots on the encircling device.

Referring now to FIGS. 39 through 42, the top cap may also include a wall 110 extending about the periphery of the top to form a container that may be filled with fusion promoting substances, including, but not limited to, osteogenic substances, osteo-conductive and or osteo-inductive substances that are naturally occurring or artificially made, bone in any of its forms, hydroxyapetite, calcium phosphate compounds, genetic material coding for bone production, bone morphogenic proteins and other as yet undiscovered bone forming agents. The embodiments may be made of bioresorbable implantable material or inert material. Referring to FIGS. 39 through 41, the wall 110 may be perforated or consist of a plurality of bars or slats 112 so that boney ingrowth may extend through the wall. The top of the container also preferably has one or more open areas for permitting boney ingrowth through the top. The container may be made of a variety of other different materials including, but not limited to, radiolucent materials with or without some radiopaque markers to allow visualization of the implantable device, or a radiopaque material.

It is appreciated that the top cap may be sized or shaped to be self-affixing to the encircling device or facet joint to prevent disengagement. If not self-affixing, it is appreciated that the top cap can be locked, affixed or otherwise attached to the facet joint, other bony spinal anatomy or the encircling device by means of a separate fixation device. The fixation device may take several forms, and may be either internal or external to the encircling device. Examples of internal fixation devices include, but are not limited to: a pin that is placed over the top of the cap which directly or indirectly engages the encircling device; or a lever that operates one or more tabs or protruding members on the top cap which engage with the encircling device. It is also appreciated that the encircling device may have the protruding members or fixation devices for fixing the top cap relative to the encircling device. Referring to FIGS.

43A through 43C, the top cap may include a pair of pegs or levers 120 that may be slid into engagement with corresponding slots or notches 122 on the encircling device 12. It is appreciated that the pegs may be manually moved or they may be resiliently biased so that when the pegs pass over the corresponding slot, the pegs will be automatically forced into the corresponding slots.

Figure 44C:
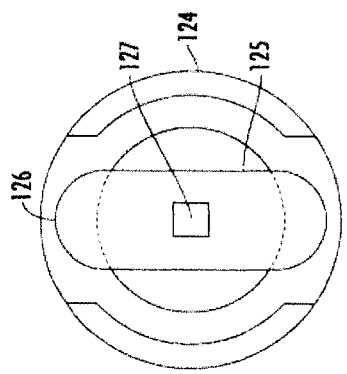
FIG. 44C is a top plan view of the encircling device and top cap of FIG. 44B showing the elongated member in the unengaged position.
Figure 44E:
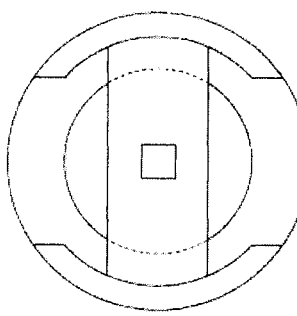
FIG. 44E is a top plan view of the encircling device and top cap of FIG. 44D with the elongated member in the engaged position.
Figure 44A:
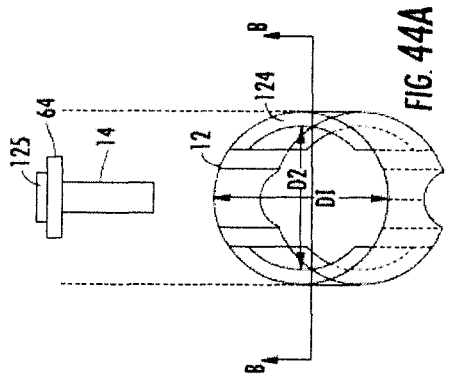
FIG. 44A is a partially exploded view of another embodiment of an encircling device and a top cap, where the encircling device has different interior diameters and an elongated member on top of the top cap.
Figure 44B:
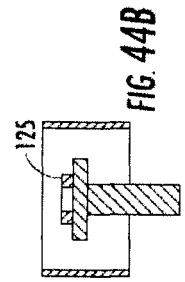
FIG. 44B is a cross-sectional view of the encircling device and top cap of FIG. 44A with the top cap inserted in the encircling device and the elongated member in an unengaged position.
Figure 44D:
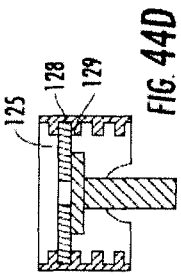
FIG. 44D is a cross-sectional view of another embodiment of a top cap with an elongated member engaging slots in the interior of the encircling device.

Alternatively, as shown in FIGS. 44A through 44C, the interior of the encircling device 12 may include a pair of additional interior walls 124 that extend partially around the interior circumference of the encircling device to create an interior with two different interior diameters D1 and D2. The top of the top cap includes an elongated member 125 having a length that is less than D1 but greater than D2. In operation, the top cap 14 and elongated member 125 are inserted into the encircling device 12 as shown in FIG. 44C. The top cap 14 is then rotated so that the ends 126 of elongated member 125 engage the interior walls 124, creating a force that acts to keep the top cap 14 and encircling device 12 in position relative to each other. The ends 126 of the elongated may be curved to facilitate engagement with the interior walls 124. Additionally, a notch or other opening 127 may be located in the elongated member to accept a corresponding tool to assist in rotating the top cap into engagement with the encircling device. It is also appreciated that the top cap may include a male member extending from the top of the elongated member to engage the female end of a corresponding tool to facilitate rotation of the top cap. Referring now to FIGS. 44D and 44E, an alternate embodiment of the encircling device having a plurality of slots 128 formed by strips 129 for accepting the elongated member 125 when it is rotated.

It is also appreciated that the fixation device may be attached or associated with the encircling device. For example, the encircling device may have, among other things, levers, pins, tangs or the like that are displaced after the top cap passes a certain point on the encircling device. Once the levers, pins or tangs are displaced, the top cap is thereafter prevented from being accidentally dislodged. In another embodiment, the encircling device may have flanges that angle into the cavity of the device or angle out of the device, and that may spring or deform away from the top cap surface as it is being passed through this section of the encircling device. After it passes this section, the flanges or the like then return to their previous position, thereby preventing back out of the top cap.

Yet another embodiment of a fixation device includes a spring that may be compressed upon insertion into the encircling device. When the spring, or the member that it is attached to passes a certain portion on the inner or outer portion of the encircling device, it extends outward to engage the encircling device or member attached thereto. Alternatively, the top cap and/or encircling device may have tabs or other extending portions that engage corresponding notches or open areas on or in the other member. The encircling device may also have a spring-action device that allows the top cap to slide past it and then spring out, preventing the top cap from backing out. Another embodiment of the fixation device is an independent spring that is inserted in a compressed mode and then expands when it reaches a groove of the encircling device. In another embodiment, when the top cap passes a point of the encircling device where the inner diameter enlarges, a spring may act to enlarge the diameter of the top cap to a size larger than the diameter of the top section thereby preventing the top cap from being removed. In another embodiment where the top cap is placed in the outer aspect of the encircling device, a compressed spring enlarges in diameter as it reaches a groove in the outer surface of the encircling device. The top cap may also be made from a resilient material that may be compressed upon insertion into the top cap having a top section with an interior diameter smaller than the top cap in its normal state. Once the top cap passes the top section of the encircling device, the interior walls have a larger diameter, thereby permitting the top cap to expand outwardly and be retained within the encircling device.

An exterior locking mechanism can also be used. For example, a pin or wedge may be placed from the exterior of the encircling device through a perforation in the encircling device to prevent backing out of the top cap. The top cap may also be affixed by compressing the encircling device or expanding the top cap in order to create contact between the components or securing the devices by interdigitating together. It is also appreciated that the top cap and the encircling device may be made of similar or different materials which may, among other things, melt together, affix together, interdigitate together, cut into each other or the like causing fixation between the structures.

Figure 45:
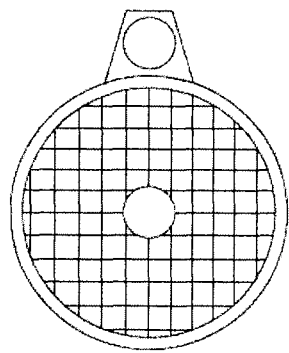
FIG. 45 is a bottom plan view of a top cap having a connector with a hole for receiving a fastener.
Figure 46:
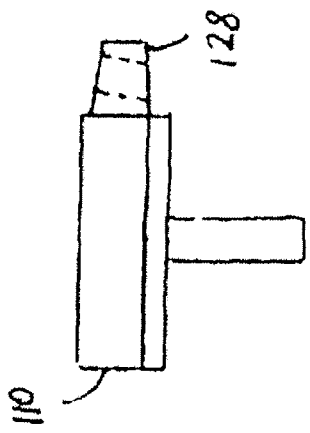
FIG. 46 is an elevated side view of the top cap of FIG. 45.
Figure 47:
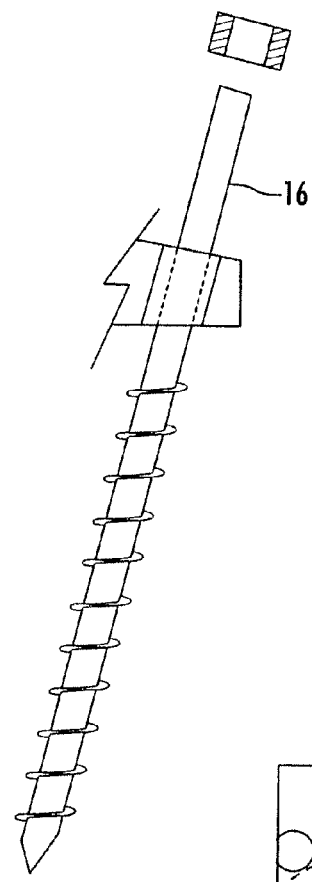
FIG. 47 is an elevated side view of an anchoring screw for a top cap.
Figure 48:
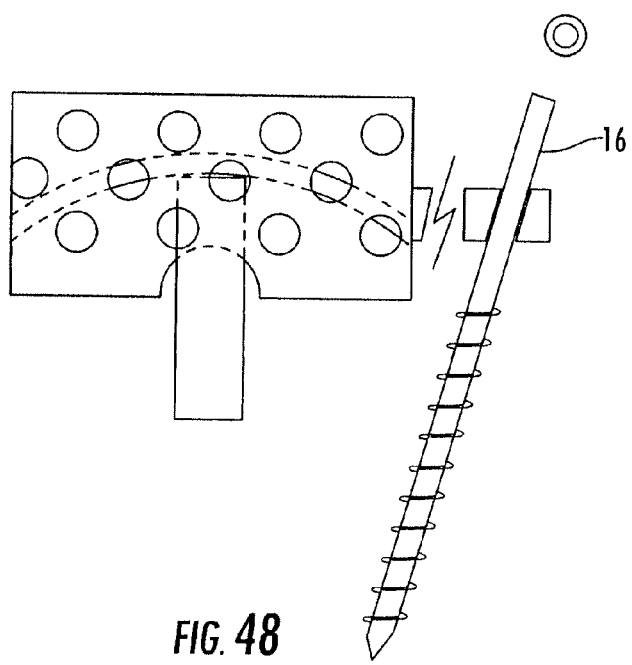
FIG. 48 is a side elevated view of an encircling device with the top cap submerged into the encircling device and an anchoring screw.

Referring now to FIGS. 45 through 47, one or more anchoring devices or attachment members 16 such as, but not limited to, spikes, screws, pegs or plugs may be used to transfix the top cap to the facet articular process, facet joint or surrounding boney structure. This screw, peg or plug may be made of a variety of different materials including, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK), or carbon filled PEEK. As shown in FIG. 1B, the fastener Referring now to FIG. 48, additional fixation of the encircling device 12 (and/or the top cap 14) may be achieved by an anchoring device or attachment member 16 inserted into a pedicle, pars interarticularis, spinous process, facet articular process, transverse process, lamina, sacral ala or other spinal bony anatomy and affixed to the encircling device 12 and/or the top cap 14. The anchoring device may be a screw, peg, plug, spikes, tang or the like that is affixed to the bone and the encircling device, and/or the top cap, through a connector on the device(s). The anchoring device may be expandable in order to obtain more bone purchase. It is also appreciated that the top cap may have a dorsal container, central shaft, anchoring attachment and a bottom encircling embodiment all connected to each other.

Referring to FIG. 1B, a retaining member 17 such as, but not limited to a nut, may be used to maintain the encircling device 12 and/or top cap 14 in position relative to the anchoring device 16 and facet.

Figure 49A:
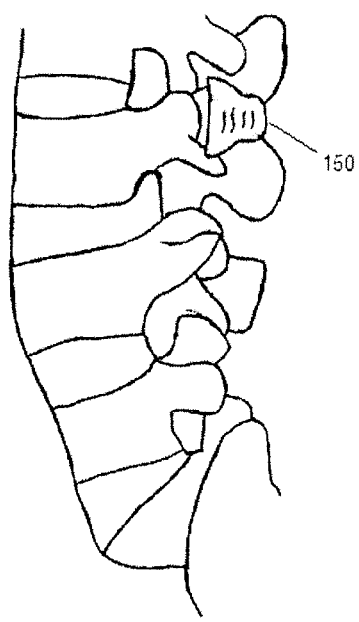
FIG. 49A is a partial elevated side view of a lumbar spine with an interspinous process spacer.
Figure 49B:
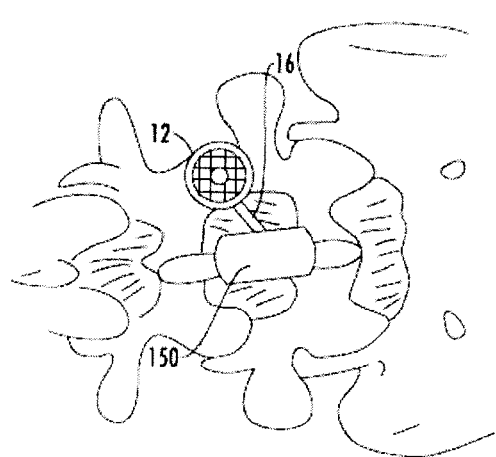
FIG. 49B is a partial elevated side view of an encircling device attached to the interspinous process spacer through a connector.
Figure 49C:
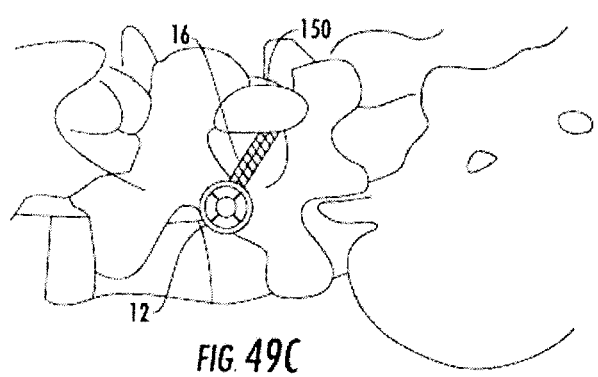
FIG. 49C is a partial elevated side view of an encircling device attached to the interspinous process spacer through a connector.

In one embodiment, a screw attached to the encircling device and/or the top cap through a connector may be placed into the pedicle adjacent to the ipsilateral facet joint that is being fused. The connector may swivel, pivot, elongate, shorten, etc. to accommodate the desired position of the anchoring screw. Once the connector is in the desired location in relation to the encircling device and/or top cap and the screw, it can be fixed in this position through a tightening mechanism or the like. The connector, which is attached to the encircling device and/or the top cap, may also be fixed with a fixed angle allowing only a certain entry of an anchoring member. Referring to FIGS. 49A through 49C, in another embodiment, the anchoring device may be a connecting rod, lever or attachment member 16 that affixes to a single pedicle screw or a interspinous process spacer 150. Overall, the anchoring fixation allows additional fixation of the encircling device and/or the top cap, thereby diminishing dislodgement or movement of the device(s).

The anchoring device may be made from a hard substance including, but not limited to, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene (SEBS-based materials and/or the like), polyetheretherketone (PEEK), or carbon filled PEEK. The anchoring device may be made of bioresorbable implant material or inert material. Amongst other things, the device may be made of radiolucent materials with or without some radiopaque makers to allow visualization of the implatable device. It may also be made of radiopaque material.

The anchoring device may take different forms. The device may be made of any solid material. The embodiment may be made of, amongst other things, a semi-rigid material, a rigid material or an adjustable/expandable/compressible material. In other embodiments, it may be made of a memory shape material that reshapes itself when introduced to a catalyst. The device may also be custom made to the patient's particular anatomy, determined by existing or future radiographic modality.

The anchoring device also may be coated with agents that promote or enhance bone growth, such as, but not limited to, bone morphogenic proteins, genetic components or hydroxyapatite. In order to promote or enhance boney growth into the device, the device(s) may be, among other things, serrated, rough, porous, perforated, meshed, textured, beaded, with protruding spikes, with ridges or and/or coated with agents that promote or enhance bone growth.

In use, the anchor device(s) may be introduced via any manner including, but not limited to, an open surgical technique, percutaneous technique, endoscopic/arthroscopic approach and/or imaging guidance technique.

Figure 52:
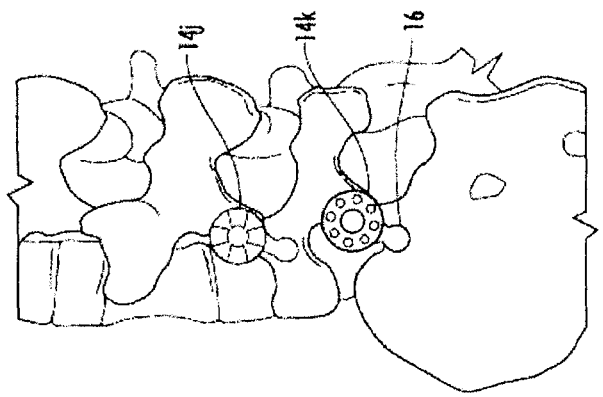
FIG. 52 is a partial perspective view of a lumbar spine with two top caps having anchoring devices.
Figure 51:
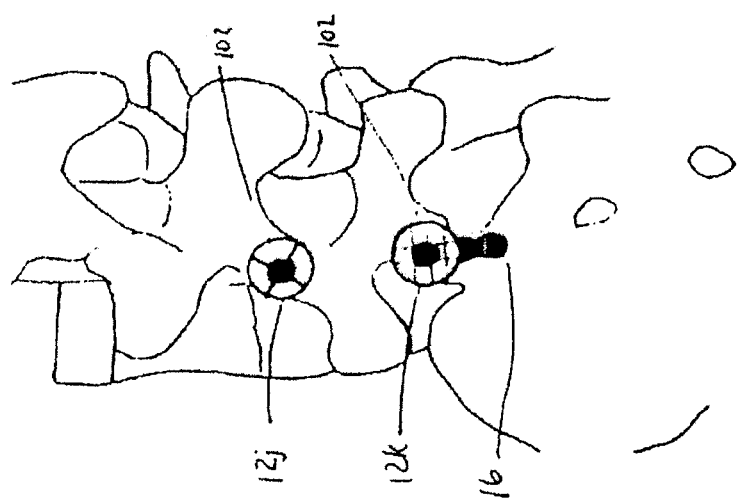
FIG. 51 is a partial perspective view of a lumbar spine with two different encircling devices, wherein the encircling device with a mesh type top cap has an anchoring screw.
Figure 50:
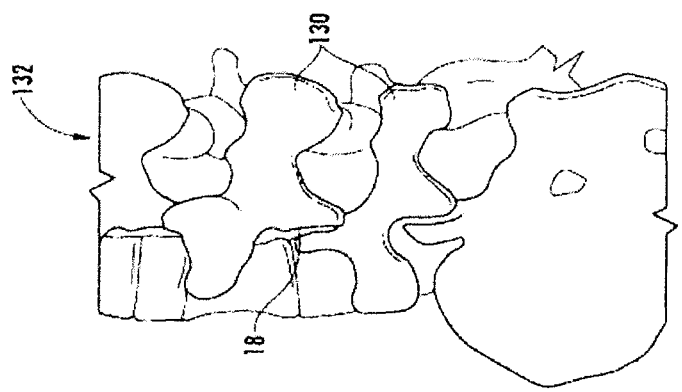
FIG. 50 is a partial perspective view of a lumbar spine.

Referring now to FIGS. 50 through 52, various exemplary embodiments of the device of the present invention are shown placed around the facet joints 18 of a vertebra 130. Referring now to FIG. 50, a view of several vertebras 130 of a lumber spine 132 is shown. FIG. 51 illustrates the use of an upper encircling device 12j in the L4-5 facet and a lower encircling device 12k in the L5-S1 facet. The lower encircling device 12k has an anchoring screw 16 connected to the device 12k for additional fixation of the device 12k. In this embodiment, both top caps have different configurations having open areas 102 to permit boney ingrowth. Similarly, FIG. 53 illustrates two examples of top caps 14j, 14k that may be used independent of encircling devices and that may utilize anchoring screws 16 for additional fixation relative to the facet joint.

Figure 53:
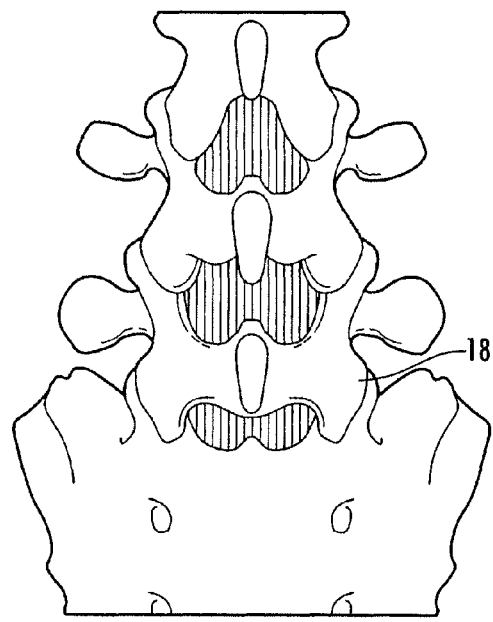
FIG. 53 is a partial elevated view of a lumbar spine.
Figure 54:
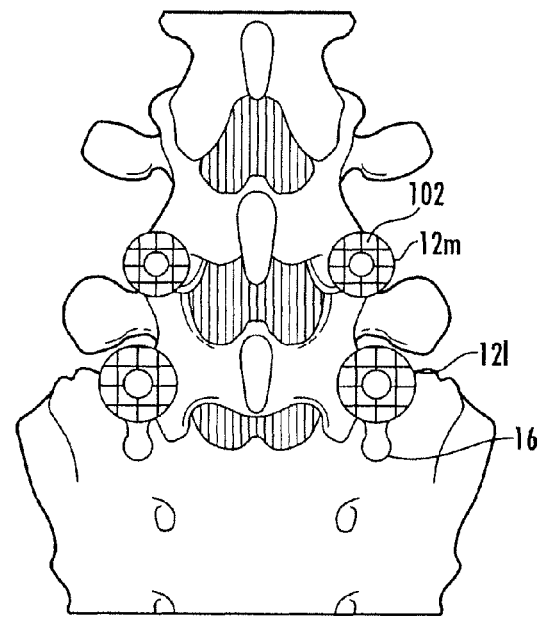
FIG. 54 is a partial elevated view of a lumbar spine having four encircling devices placed about the facet joints.

FIG. 53 illustrates another view of a lumbar spine 132, while FIG. 54 illustrates a lower pair of encircling devices 121 having anchoring screws 16 and a pair of upper encircling devices 12m placed about the facet joints 18 without the use of anchoring screws 16. In order to promote boney ingrowth, the tops of the encircling devices include grids that create open areas 102.

Figure 56:
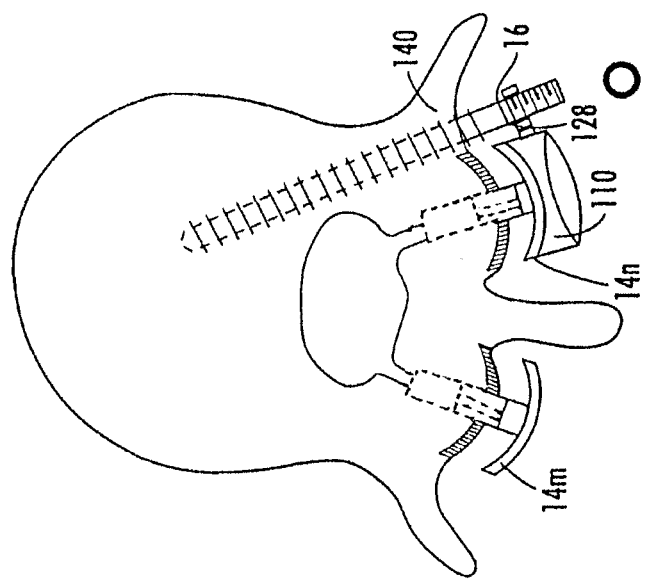
FIG. 56 is a top plan view of a vertebra with different domed top caps being placed into the facet joints, wherein one top cap has a dorsal container and an anchoring screw while the other has a central shaft. Decortication of the dorsal and peripheral facet articular process surface as well as the facet joint has been performed in preparation of a bleeding cancellous boney surface to enhance the achievement of a facet fusion.
Figure 55:
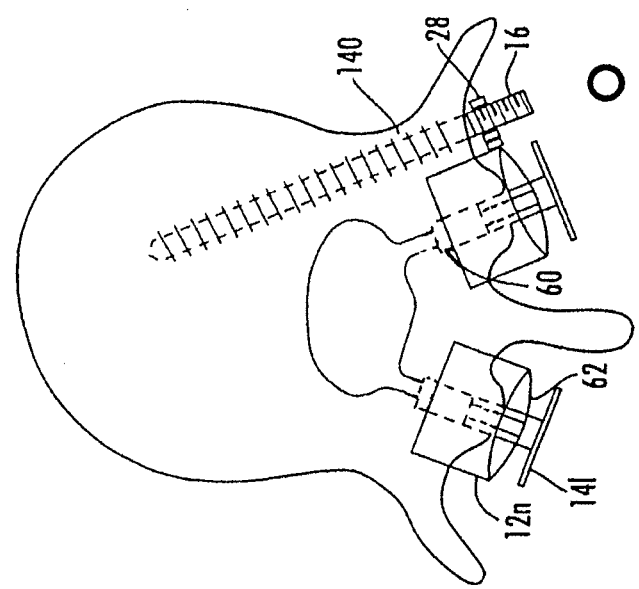
FIG. 55 is a top plan view of a vertebra with encircling devices placed around the facet joints and the top caps being driven into the pre-drilled facet joints, wherein one encircling device has an anchoring screw which has been placed through the connector of the encircling device and into the pedicle/vertebral body.
Figure 63:
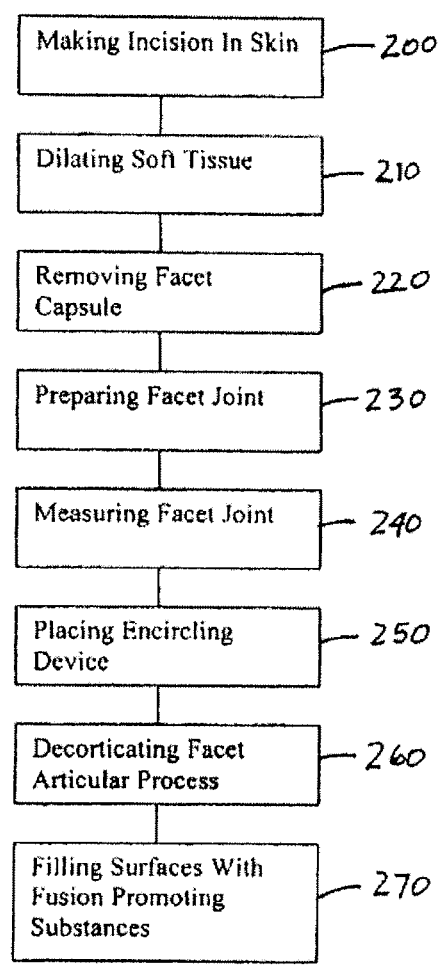
FIG. 63 illustrates an exemplary schematic flowchart of one embodiment of how the encircling device of the present invention may be introduced.

Referring now to FIG. 55, a pair of encircling devices 12n with top caps 141 is shown placed about the facet joints 18. A connector 28 extends outward from one of the encircling devices 12n to permit an anchoring screw 16 or other fastener to be placed therethrough and into the pedicle/vertebral body 140. As explained in more detail above, the shafts 62 of the top caps 141 may be inserted into holes 60 drilled in the facet joints 18. As shown in FIG. 56, it is appreciated that the top caps 14m may be used independently of encircling devices. In order to enhance boney ingrowth, it is appreciated that the top caps 14n may include a container 110 on top to hold bone graft or bone promoting substances. It is also appreciated that the dorsal and peripheral aspect of the facet joint have been decorticated to expose more surface area of bleeding cancellous bone to the top cap undersurface. The decortication may be performed in a fashion that enhances matching surface contact with the top cap. One embodiment of decorticating the facet joint is through a high speed burr in order to create a fusion bed with bleeding cancellous bone. The top caps may also include a connector 128 extending outwardly to permit an anchoring screw 16 or other fastener to be placed therethrough and into the pedicle/vertebral body 140.

FIGS. 57 through 60 illustrate a plurality of devices using top caps that may be used on the facet joints of cervical spines. Referring to FIG. 57, a matrix grid top 64a having a plurality of openings 102 for permitting boney ingrowth is placed over two cervical facet joints 18, with the two central shafts of the top caps 14o having been placed into respective holes in the facet joints 18. FIG. 58 illustrates the central shafts 62b, 62c of a pair of top caps 14p being fully inserted into the respective holes 60 of the respective facet joints 18. In this embodiment, the top cap rests on top of the lateral masses. As the central shaft is fully inserted into the facet joint, the round central shaft head 61 presses the top cap 14p onto the decorticated lateral masses. While the central shafts are illustrated as being beaded and textured with ridges, as set forth herein, it is appreciated that they may be of a variety of different configurations and not depart from the scope of the present invention. The top caps may also include a dorsal container having a plurality of posts 112 to permit boney ingrowth and increased bone supply to the fusion mass.

Additional exemplary embodiments of the configurations of the top of the tops caps 14q, 14r, 14s, 14t having open areas and different configurations 102 are shown in FIG. 59. FIG. 60 illustrates another pair of central members 62e, 100 of top caps being fully inserted into the respective holes of the facet joints. While the upper top cap 14u is shown as having a porous central shaft 62e and the lower top cap 14v is shown as having a screw 100, as set forth herein, it is appreciated that the central member may be of a variety of different fastening members and not depart from the scope of the present invention. The lower top cap 14v is also shown as having a perforated container 110 on top of the top cap 14v.

FIG. 62 illustrates a pair of perforated top caps 14w placed over the facet joints 18 of the thoracic spine shown in FIG. 61. Each top cap 14w has an articulated central shaft 62 which is placed into the corresponding hole reamed or drilled into the facet joint. When the central shaft is fully inserted into the facet joint, the round head 61, or any other configured head that is larger than the inserting hole of the top cap, of the shaft pushes the top cap into the decorticated lateral masses. Bone graft or bone promoting substances may be placed in the decorticated facet joint, and/or on top of the top cap to enhance boney growth around and through the top cap.

It is further appreciated that the top cap and/or encircling device may be utilized with an interspinous process spacer to stabilize and/or facilitate/promote fusion of the facet joint(s) by one or a combination of the following: the spacer, which may be affixed to the surrounding boney anatomy, is placed within the space between the spinous process and thus prevents motion of the two facet joints (that are intended to be fused) that adjoin the two intervened spinous processes; the spacer, which may be filled and/or coated with bone growth promoting or enhancing agents, is placed within the interspinous process space with bone growth promoting or enhancing agent to promote fusion of the interspinous process space;

and the spacer may have an attached member extending from the spacer that directly or indirectly holds the encircling device and/or top cap in relation to the facet.

Figure 65:
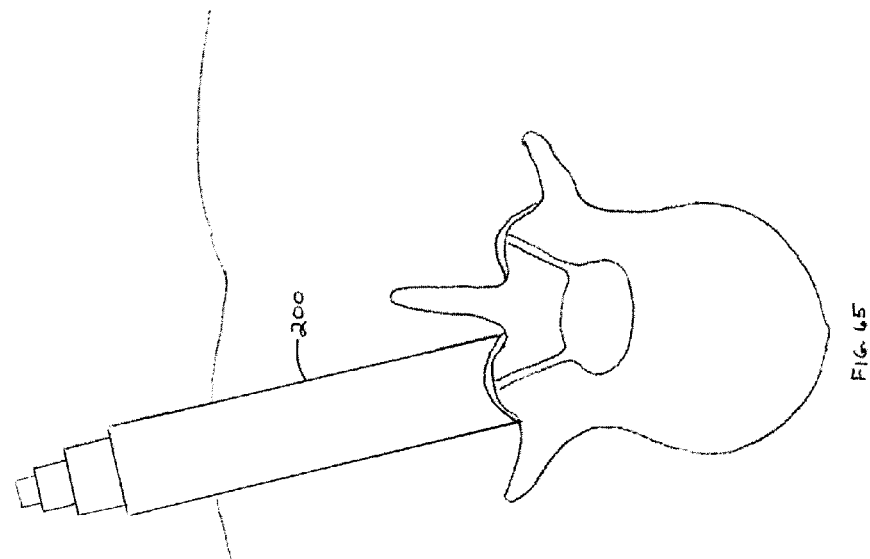
FIG. 65 is a top plan view of a vertebra illustrating the step of sequentially dilating the soft tissue with tube dilatators.
Figure 64:
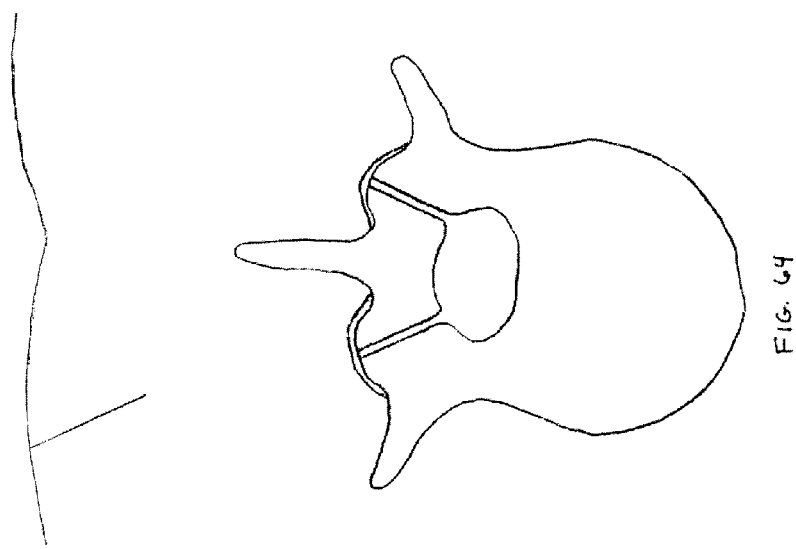
FIG. 64 is a top plan view of a vertebra with a small incision having been made in the skin over the facet joint.
Figure 67:
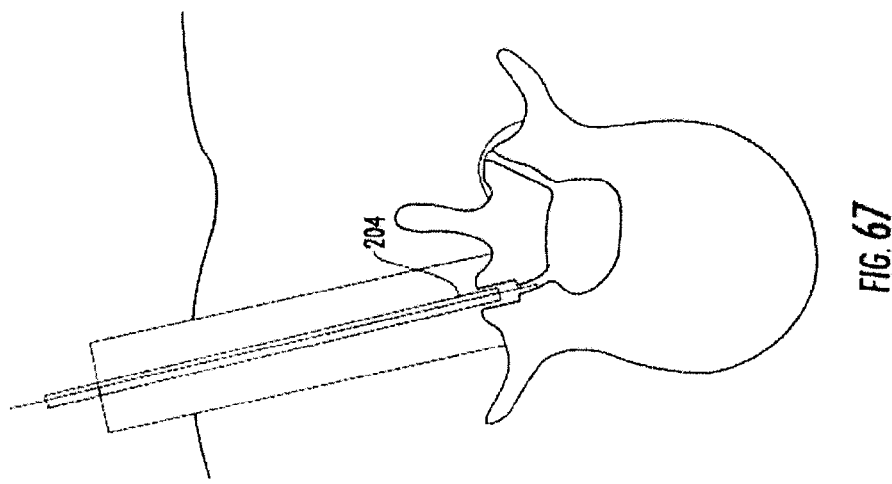
FIG. 67 is a top plan view of a vertebra illustrating the step of reaming the facet joint.
Figure 66:
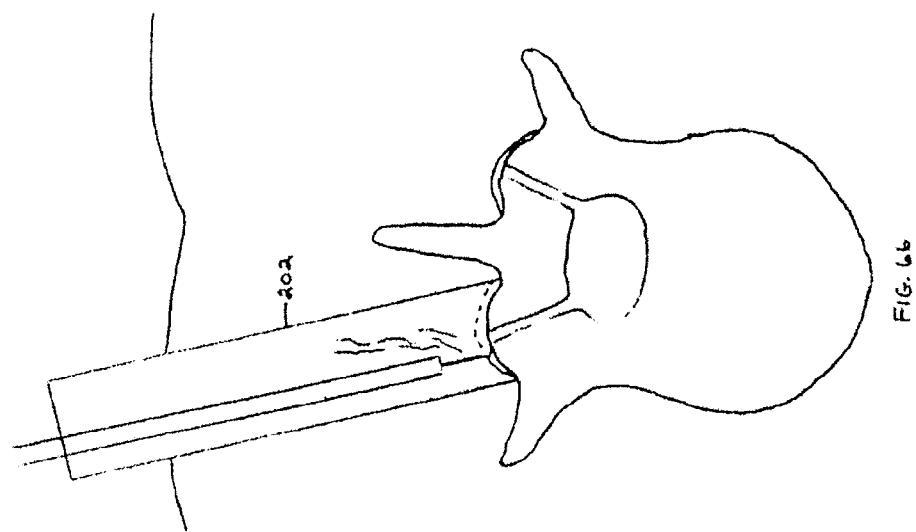
FIG. 66 is a top plan view of a vertebra illustrating the facet capsule being removed.
Figure 71:
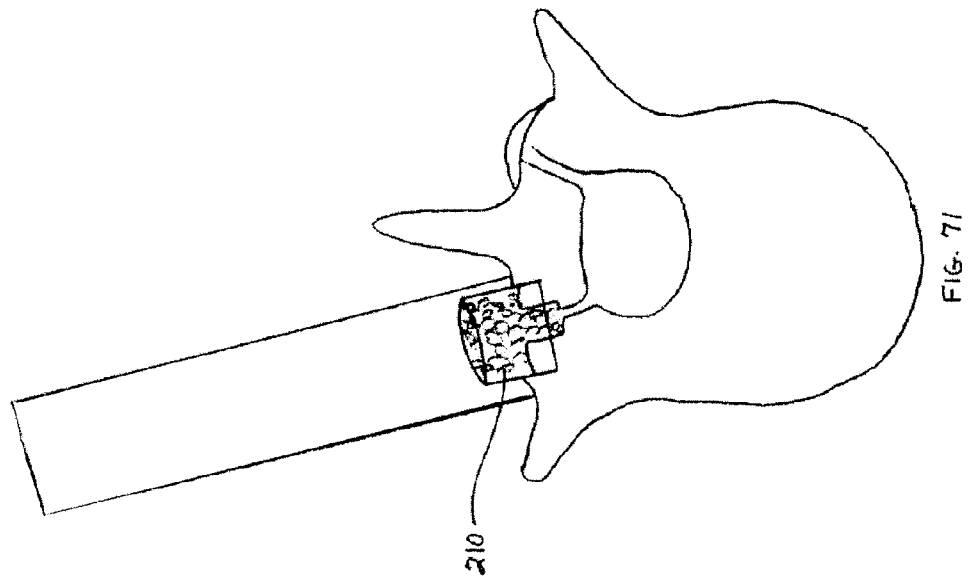
FIG. 71 is a top plan view of a vertebra showing the insertion of fusion promoting substances into the decorticated facet joint and encircling device.

It is appreciated that the device of the present invention may be introduced through a variety of different known techniques that expose the facet joint and may apply a bone growth promoting substance into the joint and surrounding tissues. As an example, referring to FIGS. 64 through 71, one technique may be performed by making a small incision in the skin over the facet joint in step 200 (FIG. 64) and sequentially dilating the soft tissues in step 210 (FIG. 65) with increasingly larger tube dilatators 200 until the appropriate size exposure is created. Then, through the final working channel 202, removal of the facet capsule is performed using electrocautery, laser or other standard trade of the art in step 220 (FIG. 66). Removing the facet capsule may allow distraction of the facet joint and indirectly open the involved neuroforamina. The facet joint is then prepared in step 230 (FIG. 67) by reaming the facet joint with a cannulated drill 204 and, in addition, removing the cartilaginous surface and decorticating the facet articular surface. Next, the size and shape of the facet joint is measured in step 240 (FIG. 68) in a known way including, but not limited to, use of a malleable cup 206 that may be placed over the facet or a series of predetermined sized facet templates to measure the facet. The encircling device 12 may then be placed around and/or into the facet joint 18 in step 250 (FIG. 69). In one embodiment, the inferior portion of the encircling device is submerged into the facet, while the top portion extends dorsal to the facet articular process. The carved areas of the encircling device are oriented to that they sit over the superior and inferior facet adjacent to the pars interarticularis above and below the intervene facet.

Figure 70:
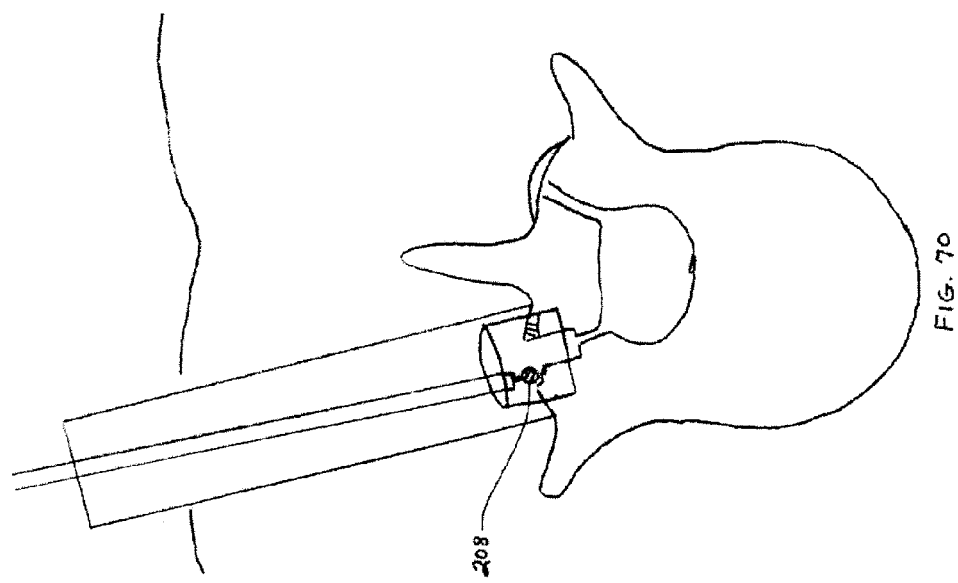
FIG. 70 is a top plan view of a vertebra illustrating the top and peripheral portion of the facet articular process being decorticated.

Next, the top and peripheral portion of the facet articular process may be decorticated by a predetermined shaped reamer 208 in step 260 (FIG. 70). It may also be decorticated by a high speed burr or other technology to expose a bleeding boney surface in step 260. This surface, along with the decorticated facet joint, can be filled in step 270 (FIG. 71) with fusion promoting substances 210, including, but not exclusive to, osteogenic substances, osteo-conductive and or osteo-inductive substances that are naturally occurring or artificially made, bone in any of its forms, hydroxyapetite, calcium phosphate compounds, genetic material coding for bone production, bone morphogenic proteins and other to be discovered bone forming agents. When placing/inserting the encircling device, there may be a stop on the inserting tool which minimizes placing the device too anteriorly and into the neuroforamina or spinal canal.

In another method, after the appropriate exposure is achieved, the capsule around the facet, but not on top of the facet joint, is removed. Then, the facet is measured and the encircling device is inserted on the facet joint. Next, the remaining capsule on top of the facet joint is removed. Thereafter, the facet joint and top of the facet joint is decorticated.

The description above is provided primarily for exemplary purposes and should not be interpreted to limit the scope of the invention. It will be understood that modifications and variations may be effected without departing from the scope of the novel concepts of the present invention, but it is understood that this application is limited only by the scope of the appended claims.

What is claimed is:

1. A device for promoting arthrodesis of a facet joint, wherein the facet joint comprises superior and inferior articular processes, the device comprising an encircling device, the encircling device including a wall defining a facet joint receiving bore such that at least part of the wall of the encircling device is adapted to extend at least partially around the superior and inferior articular processes defined by a facet capsule of the facet joint, wherein the encircling device has a top and where the device further comprises a top cap that is adapted to fit at least one of within, around or over the top of the encircling device, wherein the top cap includes a top and a top cap fixation device to facilitate affixation of the top cap to the facet, the top of the top cap includes a planar surface, at least one protruding member slidable along the planar surface and extending one of inwardly or outwardly for engaging the encircling device, the protruding member being resiliently biased.

2. The device of claim 1 wherein the encircling device has one or more open spaces to promote boney growth through the device.

3. The device of claim 1 wherein the encircling device includes a cross-sectional wall within the encircling device.

4. The device of claim 3 wherein the cross-sectional wall has a bottom and wherein the device further comprises one or more members extending from the bottom of the cross-sectional walls to facilitate fixation of the device relative to the facet joint.

5. The device of claim 1 wherein the top cap is coated with a material for promoting or enhancing bone growth.

6. The device of claim 1 wherein the top cap fixation device is chosen from the group consisting of one or more pins, ridges, protrusions, spikes, tangs, screws, pegs, tapered interference-type fit members, press fit members, springs and plugs.

7. The device of claim 1 wherein the encircling device includes an opening and wherein the fixation device includes at least one retaining member that may be inserted through the opening after the top cap is inserted into the encircling device.

8. The device of claim 1, wherein the top of the top cap includes at least one open space to promote boney growth through the device.

9. The device of claim 1, wherein the top cap fixation device is selected from the group consisting of flanges, tangs, peg or a screw.

10. The device of claim 1, wherein the top cap fixation device is a central shaft having a textured surface to promote bone growth and fixation.

11. The device of claim 1 wherein the top cap is made from a material selected from the group consisting of, bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene, polyetheretherketone, or carbon filled polyetheretherketone.

12. The device of claim 1 wherein the top cap is adapted to be self-affixing to the encircling device or facet.

13. The device of claim 1 which further comprises an attachment member for fixing the encircling device relative to the facet.

14. The device of claim 1 which further comprises an attachment member for fixing one of the top cap and encircling device relative to the facet.

15. The device of claim 14 wherein the attachment member is attached to the encircling device or top cap through a connector.

16. The device of claim 15 wherein the connector is adjustable to accommodate the desired position of the attachment member.

17. The device of claim 16 wherein the attachment member is adapted to affix to the pars interarticularis, pedicle, spinous process, transverse process, facet articular process, lamina, sacrum, sacral ala, interspinous process spacer or other spinal boney anatomy to give further fixation to the device.

18. The device of claim 15 where the connector has an opening for receiving the attachment member, wherein the opening has a fixed angle.

19. The device of claim 18 wherein the attachment member is adapted to affix to the pars interarticularis, pedicle, spinous process, transverse process, facet articular process, lamina, sacrum, sacral ala, interspinous process spacer or other spinal boney anatomy to give further fixation to the device.

20. The device of claim 1 wherein the encircling device is made from a material selected from the group consisting of bone, titanium, stainless steel, cobalt-chromium alloy, any metal alloy, a combination of metals, titanium mesh, porous tantalum, titanium alloys, carbon fiber, plastic, ultra-high molecular weight polyethylene, silicone, polyurethane, styrene-ethylene-butadiene-styrene, polyetheretherketone, or carbon filled polyetheretherketone.

21. The device of claim 1 wherein the encircling device includes a cylindrical wall.

22. The device of claim 1 wherein the top cap is perforated to promote boney growth.

23. The device of claim 1 wherein the encircling device includes a bottom side, wherein the bottom side includes carved-out areas.

24. The device of claim 1 wherein the encircling device has a surface with a texture to promote boney growth and fixation, wherein the texture of the surface is selected from the group consisting of perforated, meshed, serrated, rough, porous, textured, beaded, or of a matrix configuration.

25. The device of claim 1 wherein the encircling device cross-sectional shape is selected from the group consisting of circular, oblong, rectangular or quadrilateral.

26. The device of claim 1 wherein the encircling device further comprises means to adjust its size relative to the facet joint.

27. The device of claim 1 wherein the encircling device is coated with a bone growth or enhancing agent.

28. The device of claim 1 which further comprises an interspinous process spacer and an interspinous process spacer attachment member for affixing one of the encircling device and top cap to the interspinous process spacer.

29. The device of claim 1 which further comprises an encircling device fixation device.

30. The device of claim 29 wherein the fixation device is chosen from the group consisting of one or more pins, ridges, protrusions, spikes, tangs, screws, pegs, tapered interference-type fit members, press fit members, springs and plugs.

31. A method for promoting stabilization and fusion of a facet joint comprising the steps of:
 exposing the facet;
 providing the device of claim 1; and
 placing the encircling device such that at least part of the wall of the encircling device may be placed around the facet joint, the encircling device having an inferior portion.

32. The method of claim 31 which further comprises the step of submerging the inferior portion of the encircling device into the facet.

33. The method of claim 31 which further comprises the step of placing the top cap one of through, around or over the top of the encircling device.

34. The method of claim 33 wherein the method further comprising the steps of creating a hole in the facet and inserting the to cap fixation device of the top cap into the hole.

35. The method of claim 33 which further comprises the step of coating the top cap with a material to promote boney growth.

36. The method of claim of claim 33 which further comprises the step of attaching the top cap to the encircling device.

37. The method of claim 31 which further comprises the step of anchoring the encircling device relative to the facet.

38. A device for promoting arthrodesis of a facet joint, wherein the facet joint comprises superior and inferior articular processes each having a posterior aspect, the device comprising an encircling device, the encircling device including a wall defining a facet joint receiving bore such that at least part of the wall of the encircling device is adapted to extend at least partially around the posterior aspect of the superior and inferior articular processes defined by a facet capsule of the facet joint, wherein the encircling device has a top and where the device further comprises a top cap that is adapted to fit at least one of within, around or over the top of the encircling device, wherein the top cap includes a top and a top cap fixation device to facilitate affixation of the top cap to the facet, the top of the top cap includes a planar surface, at least one protruding member slidable along the planar surface and extending one of inwardly or outwardly for engaging the encircling device, the protruding member being resiliently biased.

* * * * *